(12) United States Patent
Biadatti et al.

(10) Patent No.: US 7,326,803 B2
(45) Date of Patent: Feb. 5, 2008

(54) LIGAND INHIBITORS OF THE RAR RECEPTORS, PROCESS FOR PREPARING SAME AND THERAPEUTIC/COSMETIC APPLICATIONS THEREOF

(75) Inventors: Thibaud Biadatti, Opio (FR); Pascal Collette, Le Cannet (FR)

(73) Assignee: Galderma Research & Development, Biot (FR)

( * ) Notice: Subject to any disclaimer, the term of this patent is extended or adjusted under 35 U.S.C. 154(b) by 303 days.

(21) Appl. No.: 10/991,430

(22) Filed: Nov. 19, 2004

(65) Prior Publication Data
US 2005/0148670 A1 Jul. 7, 2005

Related U.S. Application Data

(63) Continuation of application No. PCT/EP03/05555, filed on May 27, 2003.

(60) Provisional application No. 60/387,447, filed on Jun. 11, 2002.

(30) Foreign Application Priority Data
Jun. 4, 2002 (FR) .................................. 02 06851

(51) Int. Cl.
C07C 69/76 (2006.01)
C07C 63/33 (2006.01)
(52) U.S. Cl. ...................................... 560/102; 562/492
(58) Field of Classification Search ................ 562/426, 562/467, 459, 466, 480, 490; 560/19, 55, 560/45, 36, 51, 54; 564/171, 172, 161, 162, 564/163, 169
See application file for complete search history.

(56) References Cited
U.S. PATENT DOCUMENTS
6,103,762 A 8/2000 Bernardon et al.

(Continued)

FOREIGN PATENT DOCUMENTS
EP 0 986 537 B 3/2000

(Continued)

OTHER PUBLICATIONS

CAS online citation, 140:16571 [retrieved Aug. 25, 2007] from STN, Columbus, OH, USA.*

(Continued)

*Primary Examiner*—Karl Puttlitz
(74) *Attorney, Agent, or Firm*—Buchanan, Ingersoll & Rooney, PC

(57) ABSTRACT

Novel bicyclic compounds having the structural formula (I):

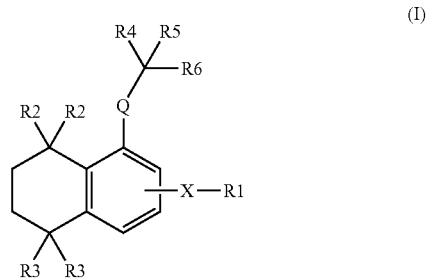

are useful in a variety of pharmaceutical applications, whether human or veterinary, and also in cosmetics.

53 Claims, 1 Drawing Sheet

U.S. PATENT DOCUMENTS

| | | |
|---|---|---|
| 6,444,709 B1 | 9/2002 | Diaz et al. |
| 6,992,094 B1 * | 1/2006 | Bernardon et al. ......... 514/350 |
| 2003/0012803 A1 | 1/2003 | Diaz et al. |
| 2003/0092758 A1 * | 5/2003 | Fesus et al. ................ 514/448 |

FOREIGN PATENT DOCUMENTS

| WO | WO 99/50239 A | 10/1999 |
|---|---|---|
| WO | WO 99/65872 A | 12/1999 |

OTHER PUBLICATIONS

International Search Report corresponding to PCT/ EP 03/05555 issued on Nov. 20, 2003, 2 pages.

* cited by examiner

LIGAND INHIBITORS OF THE RAR RECEPTORS, PROCESS FOR PREPARING SAME AND THERAPEUTIC/COSMETIC APPLICATIONS THEREOF

CROSS-REFERENCE TO PRIORITY/PCT/PROVISIONAL APPLICATIONS

This application claims priority under 35 U.S.C. § 119 of FR 02/06851, filed Jun. 4, 2002, and of provisional application Ser. No. 60/387,447, filed Jun. 11, 2002, and is a continuation of PCT/EP 2003/005555, filed May 27, 2003 and designating the United States (published in the English language on Dec. 11, 2003 as WO 2003/101945 A1), each hereby expressly incorporated by reference and each assigned to the assignee hereof.

BACKGROUND OF THE INVENTION

1. Technical Field of the Invention

The present invention relates to novel bicyclic compounds, to the process for preparing same and to a variety of applications thereof in pharmaceutical compositions for use in human or veterinary medicine, or alternatively in cosmetic compositions.

2. Description of Background and/or Related and/or Prior Art

Compounds with activity of retinoid type (vitamin A and derivatives thereof) are widely described in the literature as having activity in cell proliferation and differentiation processes. These properties provide this class of compounds high potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response elements (RARE), in the form of a heterodimer with the retinoid X receptors (known as RXRs).

Three subtypes of human RARs have been identified and described: RARα, RARβ and RARγ.

The prior art contains a large number of chemical compounds with inhibitory activity on receptors of RAR type. Among the prior art documents that may be mentioned more particularly are EP-0,986,537 which describes heteroethynylenated compounds, U.S. Pat. No. 6,103,762 which describes biaromatic compounds whose aromatic nuclei are linked via a divalent propynylene or allenylene radical, U.S. Pat. No. 6,150,413 which describes triaromatic compounds, U.S. Pat. No. 5,723,499 which describes polycyclic aromatic compounds, and U.S. Pat. No. 6,214,878 which describes stilbene compounds. U.S. Pat. No. 6,218,128 describes a family of bicyclic or tricyclic molecules.

SUMMARY OF THE INVENTION

Novel bicyclic compounds have now been developed that are inhibitors of the retinoic acid receptors.

Thus, the present invention features novel bicyclic compounds corresponding to the following general formula:

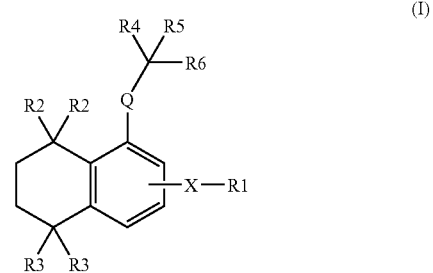

(I)

in which $R_1$ is a radical of formulae (a) to (c) below:

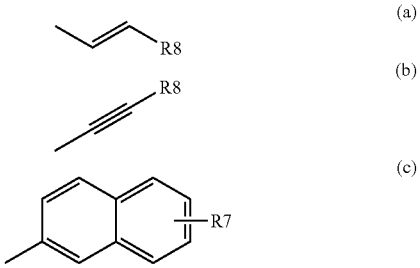

wherein $R_7$ and $R_8$ are as defined below; each of the radicals $R_2$ and $R_3$, which may be identical or different, is a hydrogen atom or an alkyl radical having from 1 to 6 carbon atoms; X is an Se atom, —CHOH, —CH$_2$ or —C=O; Q is an oxygen atom, a sulfur atom, CH$_2$, —NH or —NR$_9$—, wherein $R_9$ is as defined below; $R_4$ and $R_5$, which may be identical or different, are each a hydrogen atom, an alkyl radical having from 1 to 6 carbon atoms, or together form an oxo radical; $R_6$ is a phenyl radical, a naphthyl radical or a heterocyclic radical, $R_6$ being optionally substituted with one or more radicals selected from among an alkyl radical having from 1 to 6 carbon atoms, an —OR$_{10}$ radical, a halogen atom, —CF$_3$, —NH$_2$ and a nitrogen atom mono- or disubstituted with an alkyl radical having from 1 to 6 carbon atoms, wherein $R_{10}$ is as defined below; $R_7$ is a radical —COR$_{11}$, wherein $R_{11}$ is as defined below, $R_8$ is a radical:

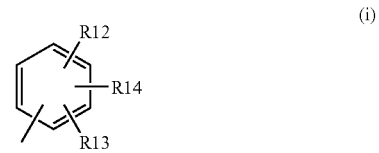

(i)

wherein $R_{12}$, $R_{13}$ and $R_{14}$ are as defined below; $R_{10}$ is an alkyl radical having from 1 to 6 carbon atoms; $R_{10}$ is a hydrogen atom or an alkyl radical having from 1 to 6 carbon atoms; $R_{11}$ is a radical —OR$_{15}$ or a radical —NR$_{15}$R$_{16}$, wherein $R_{15}$ and $R_{16}$ are as defined below; $R_{12}$ and $R_{13}$, which may be identical or different, are each a hydrogen atom, a halogen atom, an alkyl radical having from 1 to 6 carbon atoms or a radical —OR$_{17}$, wherein $R_{17}$ is as defined below; $R_{14}$ is a radical —COR$_{18}$, wherein $R_{18}$ is as defined below; $R_{15}$, $R_{16}$ and $R_{17}$, which may be identical or different, are each a hydrogen atom or an alkyl radical having from 1 to 6 carbon atoms; $R_{18}$ is a radical —OR$_{19}$, or a radical —NR$_{19}$R$_{20}$, wherein R$_{19}$ and R$_{20}$ are as defined below; R$_{19}$ is a hydrogen atom or an alkyl radical having from 1 to 6 carbon atoms; R$_{20}$ is a hydrogen atom, an alkyl radical having from 1 to 6 carbon atoms, or —OH, and the optical isomers and salts thereof obtained with a pharmaceutically acceptable salt or base, and also mixtures of said compounds of formula (I).

BRIEF DESCRIPTION OF THE DRAWING

The FIGURE of Drawing illustrates various reaction mechanisms for the preparation of the compounds of the invention.

DETAILED DESCRIPTION OF BEST MODE AND SPECIFIC/PREFERRED EMBODIMENTS OF THE INVENTION

Figure 1:
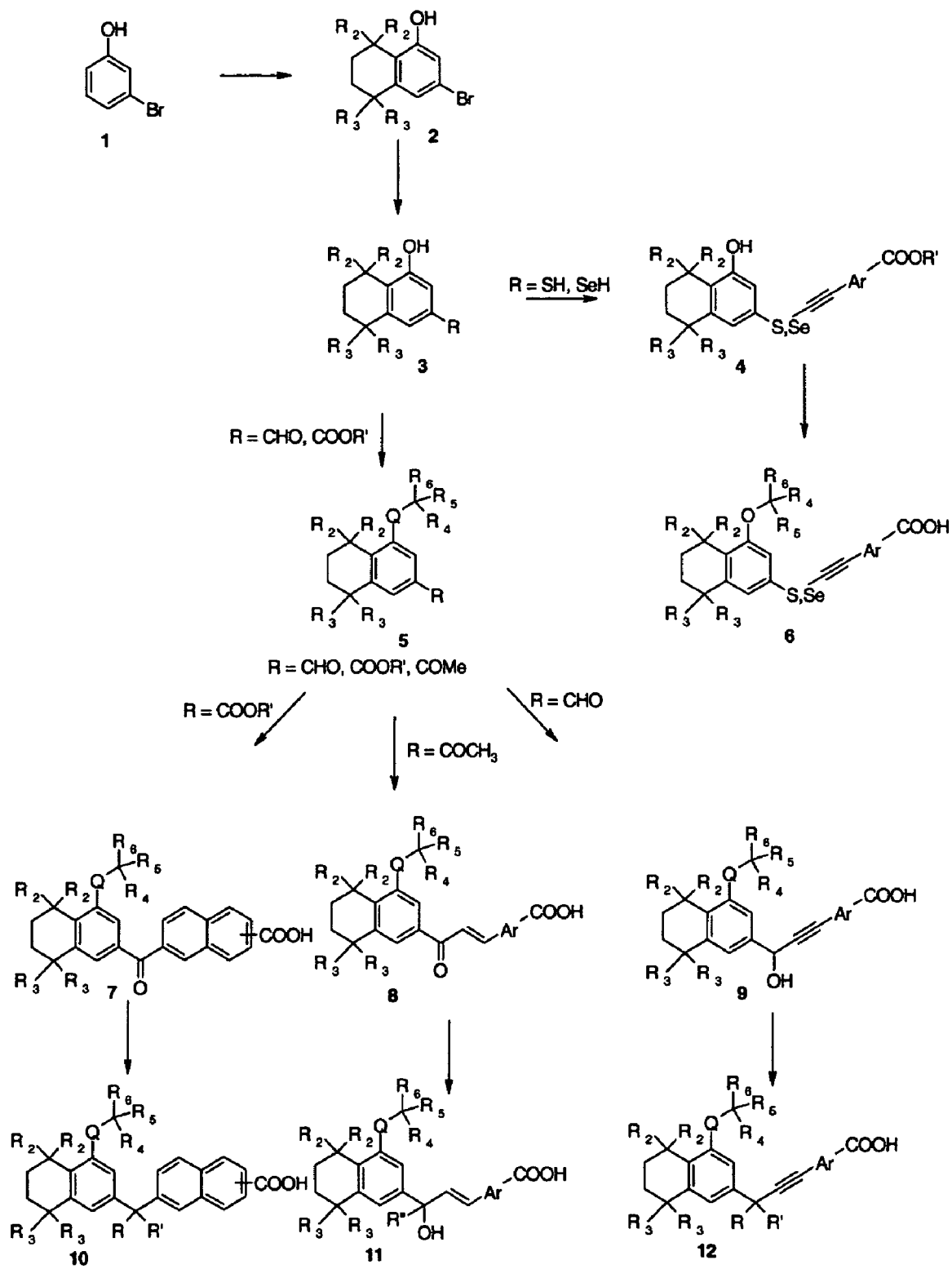

When the compounds according to the invention are in the form of a salt, it is preferably an alkali metal or alkaline-earth metal salt, or alternatively a zinc salt, or an organic amine salt.

According to the present invention:

The expression "alkyl radical having from 1 to 6 carbon atoms" preferably means the methyl, ethyl, propyl, isopropyl, butyl, tert-butyl, pentyl, or hexyl radicals.

The term "halogen atom" preferably means a fluorine, chlorine, or bromine atom.

The term "heterocycle" means a carbon-based ring of 5 to 8 carbon atoms interrupted with 1 or 2 hetero atoms selected from among sulfur, nitrogen, oxygen and selenium, and preferably a pyridine, pyrimidine or thiophene radical.

Among the compounds corresponding to the general formula (I) above that may be mentioned are the following, alone or in admixture:

4-[4-(3-fluorobenzyloxy)-5,5,8,8-tetramethyl-5,6,7,8-tetrahydro-2-naphthylselanylethynyl]benzoic acid, 4-[5,5,8,8-tetramethyl-4-(4-methylbenzyloxy)-5,6,7,8-tetrahydro-2-naphthylselanylethynyl]benzoic acid, 4-[4-(4-tert-butylbenzyloxy)-5,5,8,8-tetramethyl-5,6,7,8,-tetrahydro-2-naphthylselanylethynyl]benzoic acid, 4-[4-(3,4-difluorobenzyloxy)-5,5,8,8-tetramethyl-5,6,7,8-tetrahydro-2-naphthylselanylethynyl]benzoic acid, 4-[4-(2,4-difluorobenzyloxy)-5,5,8,8-tetramethyl-5,6,7,8-tetrahydro-2-naphthylselanylethynyl]benzoic acid, 4-[5,5,8,8-tetramethyl-4-(4-trifluoromethylbenzyloxy)-5,6,7,8-tetrahydro-2-naphthylselanylethynyl]benzoic acid, 4-[5,5,8,8-tetramethyl-4-(2-naphthylmethoxy)-5,6,7,8-tetrahydro-2-naphthylselanylethynyl]benzoic acid, 4-[4-(4-chlorobenzyloxy)-5,5,8,8-tetramethyl-5,6,7,8-tetrahydro-2-naphthylselanylethynyl]benzoic acid, 4-[4-(4-bromobenzyloxy)-5,5,8,8-tetramethyl-5,6,7,8-tetrahydro-2-naphthylselanylethynyl]benzoic acid, 4-[5,5,8,8-tetramethyl-4-(3-methylbenzyloxy)-5,6,7,8-tetrahydro-2-naphthylselanylethynyl]benzoic acid, 4-[4-(4-fluorobenzyloxy)-5,5,8,8-tetramethyl-5,6,7,8-tetrahydro-2-naphthylselanylethynyl]benzoic acid, 4-{3-hydroxy-3-[5,5,8,8-tetramethyl-4-(4-trifluoromethylbenzyloxy)-5,6,7,8-tetrahydro-2-naphthyl]prop-1-ynyl}benzoic acid, 4-{3-hydroxy-3-[5,5,8,8-tetramethyl-4-(4-tert-butylbenzyloxy)-5,6,7,8-tetrahydro-2-naphthyl]prop-1-ynyl}benzoic acid, 4-{3-hydroxy-3-[5,5,8,8-tetramethyl-4-(4-methylbenzyloxy)-5,6,7,8-tetrahydro-2-naphthyl]prop-1-ynyl}benzoic acid, 4-{3-[4-(4-tert-butylbenzyloxy)-5,5,8,8-tetramethyl-5,6,7,8-tetrahydro-2-naphthyl]-3-hydroxyprop-1-ynyl}benzoic acid, 4-{(E)-3-[4-(4-fluorobenzyloxy)-5,5,8,8-tetramethyl-5,6,7,8-tetrahydro-2-naphthyl]-3-oxopropenyl}benzoic acid, 6-{1-[4-(4-fluorobenzyloxy)-5,5,8,8-tetramethyl-5,6,7,8-tetrahydro-2-naphthyl]methanoyl}naphthalene-2-carboxylic acid, 6-{1-[4-(4-fluorobenzyloxy)-5,5,8,8-tetramethyl-5,6,7,8-tetrahydro-2-naphthyl]-1-hydroxymethyl}naphthalene-2-carboxylic acid, 4-{3-[4-(4-fluorobenzylamino)-5,5,8,8-tetramethyl-5,6,7,8-tetrahydro-2-naphthyl]-3-hydroxypropenyl}benzoic acid, 4-(3-{4-[(4-fluorobenzyl)methylamino]-5,5,8,8-tetramethyl-5,6,7,8-tetrahydro-2-naphthyl}-3-oxopropenyl)benzoic acid, 4-{3-[4-(4-fluorobenzylamino)-5,5,8,8-tetramethyl-5,6,7,8-tetrahydro-2-naphthyl]-3-hydroxyprop-1-ynyl}benzoic acid, 4-{3-[4-(4-fluorobenzylamino)-5,5,8,8-tetramethyl-5,6,7,8-tetrahydro-2-naphthyl]-3-oxopropenyl}benzoic acid, 4-(3-{4-[(4-fluorobenzyl)methylamino]-5,5,8,8-tetramethyl-5,6,7,8-tetrahydro-2-naphthyl}-3-hydroxypropenyl)benzoic acid, 4-(3-{4-[(4-fluorobenzyl)methylamino]-5,5,8,8-tetramethyl-5,6,7,8-tetrahydro-2-naphthyl}-3-hydroxyprop-1-ynyl)benzoic acid, 4-{3-[4-(4-fluorobenzylsulfanyl)-5,5,8,8-tetramethyl-5,6,7,8-tetrahydro-2-naphthyl]-3-hydroxypropenyl}benzoic acid, 4-{3-[4-(4-fluorobenzylsulfanyl)-5,5,8,8-tetramethyl-5,6,7,8-tetrahydro-2-naphthyl]-3-oxopropenyl}benzoic acid, 4-{3-[4-(4-fluorobenzylsulfanyl)-5,5,8,8-tetramethyl-5,6,7,8-tetrahydro-2-naphthyl]-3-hydroxyprop-1-ynyl}benzoic acid, 4-{3-[4-(4-fluorobenzylamino)-5,5,8,8-tetramethyl-5,6,7,8-tetrahydro-2-naphthyl]-3-hydroxypropenyl}-2-hydroxybenzoic acid, 4-(3-{4-[(4-fluorobenzyl)methylamino]-tetramethyl-5,6,7,8-tetrahydro-2-naphthyl}oxopropenyl)-2-hydroxybenzoic acid, 4-{3-[4-(4-fluorobenzylamino)-5,5,8,8-tetramethyl-5,6,7,8-tetrahydro-2-naphthyl]-3-hydroxyprop-1-ynyl}-2-hydroxybenzoic acid, 4-{3-[4-(4-fluorobenzylamino)-5,5,8,8-tetramethyl-5,6,7,8-tetrahydro-2-naphthyl]-3-oxopropenyl}-2-hydroxybenzoic acid, 4-(3-{4-[(4-fluorobenzyl)methylamino]-5,5,8,8-tetramethyl-5,6,7,8-tetrahydro-2-naphthyl}-3-hydroxypropenyl)-2-hydroxybenzoic acid, 4-(3-{4-[(4-fluorobenzyl)methylamino]-5,5,8,8-tetramethyl-5,6,7,8-tetrahydro-2-naphthyl}-3-hydroxyprop-1-ynyl)-2-hydroxybenzoic acid, 4-{3-[4-(4-fluorobenzylsulfanyl)-5,5,8,8-tetramethyl-5,6,7,8-tetrahydro-2-naphthyl]-3-hydroxypropenyl}-2-hydroxybenzoic acid, 4-{3-[4-(4-fluorobenzylsulfanyl)-5,5,8,8-tetramethyl-5,6,7,8-tetrahydro-2-naphthyl]-3-oxopropenyl}-2-hydroxybenzoic acid, 4-{3-[4-(4-fluorobenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-fluorobenzyloxy)-5,5,8,8-tetramethyl-5,6,7,8-tetrahydro-2-naphthyl]-3-hydroxypropenyl}-2-hydroxybenzoic acid, 4-{3-[4-(4-fluorobenzyloxy)-5,5,8,8-tetramethyl-5,6,7,8-tetrahydro-2-naphthyl]-3-oxopropenyl}-2-hydroxybenzoic acid, 4-{3-[4-(4-fluorobenzyloxy)-5,5,8,8-tetramethyl-5,6,7,8-tetrahydro-2-naphthyl]-3-hydroxyprop-1-ynyl}-2-hydroxybenzoic acid, 4-{3-[4-(4-fluorobenzoylamido)-5,5,8,8-tetramethyl-5,6,7,8-tetrahydro-2-naphthyl]-3-hydroxypropenyl}benzoic acid, 4-(3-{4-[(4-fluoro)methylbenzoylamido]-5,5,8,8-tetramethyl-5,6,7,8-tetrahydro-2-naphthyl}-3-oxopropenyl)benzoic acid, 4-{3-[4-(4-fluorobenzoylamido)-5,5,8,8-tetramethyl-5,6,7,8-tetrahydro-2-naphthyl]-3-hydroxyprop-1-ynyl}benzoic acid, 4-(3-{4-[(4-fluoro)methylbenzoylamido]-5,5,8,8-tetramethyl-5,6,7,8-tetrahydro-2-naphthyl}-3-hydroxypropenyl)benzoic acid, 4-{3-[4-(4-fluorobenzoylamido)-5,5,8,8-tetramethyl-5,6,7,8-tetrahydro-2-naphthyl]-3-oxopropenyl}benzoic acid, 4-(3-{4-[(4-fluoro)methylbenzoylamido]-5,5,8,8-tetramethyl-5,6,7,8-tetrahydro-2-naphthyl}hydroxyprop-1-ynyl)benzoic acid, 4-(3-{4-[1-(4-fluorophenyl)-1-methylethoxy]-5,5,8,8-tetramethyl-5,6,7,8-tetrahydro-2-naphthyl}-3-hydroxypropenyl)benzoic acid, 4-(3-{4-[1-(4-fluorophenyl)-1-methylethoxy]-5,5,8,8-tetramethyl-5,6,7,8-tetrahydro-2-naphthyl}-3-oxopropenyl)benzoic acid, 4-(3-{4-[1-(4-fluorophenyl)-1-methylethoxy]-5,5,8,8-tetramethyl-5,6,7,8-tetrahydro-2-naphthyl}-3-hydroxyprop-1-ynyl)benzoic acid, 4-{3-[4-(4-methylbenzylamino)-5,5,8,8-tetramethyl-5,6,7,8-tetrahydro-2-naphthyl]-3-hydroxypropenyl}benzoic acid, 4-(3-{4-[(4-methylbenzyl)methylamino]-5,5,8,8-tetramethyl-5,6,7,8-tetrahydro-2-naphthyl}-3-oxopropenyl)benzoic acid, 4-{3-[4-(4-methylbenzylamino)-5,5,8,8-tetramethyl-5,6,7,8-tetrahydro-2-naphthyl]-3-hydroxyprop-1-ynyl}benzoic acid, 4-{3-[4-(4-methylbenzylamino)-5,5,8,8-tetramethyl-5,6,7,8-tetrahydro-2-naphthyl]-3-oxopropenyl}benzoic acid, 4-(3-{4-[(4-methylbenzyl)methylamino]-5,5,8,8-tetramethyl-5,6,7,8-tetrahydro-2-naphthyl}-3-hydroxypropenyl)benzoic acid, 4-(3-{4-[(4-methylbenzyl)methylamino]-5,5,8,8-tetramethyl-5,6,7,8-tetrahydro-2-naphthyl}-3-hydroxyprop-1-ynyl)benzoic acid, 4-{3-[4-(4-methylbenzylsulfanyl)-5,5,8,8-tetramethyl-5,6,7,8-tetrahydro-2-naphthyl]-3-hydroxypropenyl}benzoic acid, 4-{3-[4-(4-methylbenzylsulfanyl)-5,5,8,8-tetramethyl-5,6,7,8-tetrahydro-2-naphthyl]-3-oxopropenyl}benzoic acid, 4-{3-[4-(4-methylbenzylsulfanyl)-5,5,8,8-tetramethyl-5,6,7,8-tetrahydro-2-naphthyl]-3-hydroxyprop-1-ynyl}benzoic acid, 4-{3-[4-(4-methylbenzylamino)-5,5,8,8-tetramethyl-5,6,7,8-tetrahydro-2-naphthyl]-3-hydroxypropenyl}-2-hydroxybenzoic acid, 4-(3-{4-[(4-methylbenzyl)methylamino]-5,5,8,8-tetramethyl-5,6,7,8-tetrahydro-2-naphthyl}-3-oxopropenyl)-2-hydroxybenzoic acid, 4-{3-[4-(4-methylbenzylamino)-5,5,8,8-tetramethyl-5,6,7,8-tetrahydro-2-naphthyl]-3-hydroxyprop-1-ynyl}-2-hydroxybenzoic acid, 4-{3-[4-(4-methylbenzylamino)-5,5,8,8-tetramethyl-5,6,7,8-tetrahydro-2-naphthyl]-3-oxopropenyl}-2-hydroxybenzoic acid, 4-(3-{4-[(4-methylbenzyl)methylamino]-5,5,8,8-tetramethyl-5,6,7,8-tetrahydro-2-naphthyl}-3-hydroxypropenyl)-2-hydroxybenzoic acid, 4-(3-{4-[(4-methylbenzyl)methylamino]-5,5,8,8-tetramethyl-5,6,7,8-tetrahydro-2-naphthyl}-3-hydroxyprop-1-ynyl)-2-hydroxybenzoic acid, 4-{3-[4-(4-methylbenzylsulfanyl)-5,5,8,8-tetramethyl-5,6,7,8-tetrahydro-2-naphthyl]-3-hydroxypropenyl}-2-hydroxybenzoic acid, 4-{3-[4-(4-methylbenzylsulfanyl)-5,5,8,8-tetramethyl-5,6,7,8-tetrahydro-2-naphthyl]-3-oxopropenyl}-2-hydroxybenzoic acid, 4-{3-[4-(4-methylbenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-methylbenzyloxy)-5,5,8,8-tetramethyl-5,6,7,8-tetrahydro-2-naphthyl]-3-hydroxypropenyl}-2-hydroxybenzoic acid, 4-{3-[4-(4-methylbenzyloxy)-5,5,8,8-tetramethyl-5,6,7,8-tetrahydro-2-naphthyl]-3-oxopropenyl}-2-hydroxybenzoic acid, 4-{3-[4-(4-methylbenzyloxy)-5,5,8,8-tetramethyl-5,6,7,8-tetrahydro-2-naphthyl]-3-hydroxyprop-1-ynyl}-2-hydroxybenzoic acid, 4-[3-(4-{[1-(4-methylphenyl)methanoyl]amino}-5,5,8,8-tetramethyl-5,6,7,8-tetrahydro-2-naphthyl)-3-hydroxypropenyl]benzoic acid, 4-[3-(4-{[1-(4-methylphenyl)methanoyl]methylamino}-5,5,8,8-tetramethyl-5,6,7,8-tetrahydro-2-naphthyl)-3-oxopropenyl]benzoic acid, 4-[3-(4-{[1-(4-methylphenyl)methanoyl]amino}-5,5,8,8-tetramethyl-5,6,7,8-tetrahydro-2-naphthyl)-3-hydroxyprop-1-ynyl]benzoic acid, 4-[3-(4-{[1-(4-methylphenyl)methanoyl]methylamino}-5,5,8,8-tetramethyl-5,6,7,8-tetrahydro-2-naphthyl)-3-hydroxypropenyl]benzoic acid, 4-[3-(4-{[1-(4-methylphenyl)methanoyl]amino}-5,5,8,8-tetramethyl-5,6,7,8 -tetrahydro-2-naphthyl)-3-oxopropenyl]benzoic acid, 4-[3-(4-{[1-(4-4-methylphenyl)methanoyl]methylamino}-5,5,8,8-tetramethyl-5,6,7,8-tetrahydro-2-naphthyl)-3-hydroxyprop-1-ynyl]benzoic acid, 4-(3-{4-[1-(4-methylphenyl)-1-methylethoxy]-5,5,8,8-tetramethyl-5,6,7,8-tetrahydro-2-naphthyl}-3-hydroxypropenyl)benzoic acid, 4-(3-{4-[1-(4-methylphenyl)-1-methylethoxy]-5,5,8,8-tetramethyl-5,6,7,8-tetrahydro-2-naphthyl}-3-oxopropenyl)benzoic acid, 4-(3-{4-[1-(4-methylphenyl)-1-methylethoxy]-5,5,8,8-tetramethyl-5,6,7,8-tetrahydro-2-naphthyl}-3-hydroxyprop-1-ynyl)benzoic acid, 4-{3-[4-(4-dimethylaminobenzylamino)-5,5,8,8-tetramethyl-5,6,7,8-tetrahydro-2-naphthyl]-3-hydroxypropenyl}benzoic acid, 4-(3-{4-[(4-dimethylaminobenzyl)methylamino]-5,5,8,8-tetramethyl-5,6,7,8-tetrahydro-2-naphthyl}-3-oxopropenyl)benzoic acid, 4-{3-[4-(4-dimethylaminobenzylamino)-5,5,8,8-tetramethyl-5,6,7,8-tetrahydro-2-naphthyl]-3-hydroxyprop-1-ynyl}benzoic acid, 4-{3-[4-(4-dimethylaminobenzylamino)-5,5,8,8-tetramethyl-5,6,7,8-tetrahydro-2-naphthyl]-3-oxopropenyl}benzoic acid, 4-(3-{4-[(4-dimethylaminobenzyl)methylamino]-5,5,8,8-tetramethyl-5,6,7,8-tetrahydro-2-naphthyl}-3-hydroxypropenyl)benzoic acid, 4-(3-{4-[(4-dimethylaminobenzyl)methylamino]-5,5,8,8-tetramethyl-5,6,7,8-tetrahydro-2-naphthyl}-3-hydroxyprop-1-ynyl)benzoic acid, 4-{3-[4-(4-dimethylaminobenzylsulfanyl)-5,5,8,8-tetramethyl-5,6,7,8-tetrahydro-2-naphthyl]-3-hydroxypropenyl}benzoic acid, 4-{3-[4-(4-dimethylaminobenzylsulfanyl)-5,5,8,8-tetramethyl-5,6,7,8-tetrahydro-2-naphthyl]-3-oxopropenyl}benzoic acid, 4-{3-[4-(4-dimethylaminobenzylsulfanyl)-5,5,8,8-tetramethyl-5,6,7,8-tetrahydro-2-naphthyl]-3-hydroxyprop-1-ynyl}benzoic acid, 4-{3-[4-(4-dimethylaminobenzylamino)-5,5,8,8-tetramethyl-5,6,7,8-tetrahydro-2-naphthyl]-3-hydroxypropenyl}-2-hydroxybenzoic acid, 4-(3-{4-[(4-dimethylaminobenzyl)methylamino]-5,5,8,8-tetramethyl-5,6,7,8-tetrahydro-2-naphthyl}-3-oxopropenyl)-2-hydroxybenzoic acid, 4-{3-[4-(4-dimethylaminobenzylamino)-5,5,8,8-tetramethyl-5,6,7,8-tetrahydro-2-naphthyl]-3-hydroxyprop-1-ynyl}-2-hydroxybenzoic acid, 4-{3-[4-(4-dimethylaminobenzylamino)-5,5,8,8-tetramethyl-5,6,7,8-tetrahydro-2-naphthyl]-3-oxopropenyl}-2-hydroxybenzoic acid, 4-(3-{4-[(4-dimethylaminobenzyl)methylamino]-5,5,8,8-tetramethyl-5,6,7,8-tetrahydro-2-naphthyl}-3-hydroxypropenyl)-2-hydroxybenzoic acid, 4-(3-{4-[(4-dimethylaminobenzyl)methylamino]-5,5,8,8-tetramethyl-5,6,7,8-tetrahydro-2-naphthyl}-3-hydroxyprop-1-ynyl)-2-hydroxybenzoic acid, 4-{3-[4-(4-dimethylaminobenzylsulfanyl)-5,5,8,8-tetramethyl-5,6,7,8-tetrahydro-2-naphthyl]-3-hydroxypropenyl}-2-hydroxybenzoic acid, 4-{3-[4-(4-dimethylaminobenzylsulfanyl)-5,5,8,8-tetramethyl-5,6,7,8-tetrahydro-2-naphthyl]-3-oxopropenyl}-2-hydroxybenzoic acid, 4-{3-[4-(4-dimethylaminobenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-dimethylaminobenzyloxy)-5,5,8,8-tetramethyl-5,6,7,8-tetrahydro-2-naphthyl]-3-hydroxypropenyl}-2-hydroxybenzoic acid, 4-{3-[4-(4-dimethylaminobenzyloxy)-5,5,8,8-tetramethyl-5,6,7,8-tetrahydro-2-naphthyl]-3-oxopropenyl}-2-hydroxybenzoic acid, 4-{3-[4-(4-dimethylaminobenzyloxy)-5,5,8,8-tetramethyl-5,6,7,8-tetrahydro-2-naphthyl]-3-hydroxyprop-1-ynyl}-2-hydroxybenzoic acid, 4-[3-(4-{[1-(4-dimethylaminophenyl)methanoyl]amino}-5,5,8,8-tetramethyl-5,6,7,8-tetrahydro-2-naphthyl)-3-hydroxypropenyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-oxopropenyl]benzoic acid, 4-[3-(4-{[1-(4-dimethylaminophenyl)methanoyl]amino}-5,5,8,8-tetramethyl-5,6,7,8-tetrahydro-2-naphthyl)-3-hydroxyprop-1-ynyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-hydroxypropenyl]benzoic acid, 4-[3-(4-{[1-(4-dimethylaminophenyl)methanoyl]amino}-5,5,8,8-tetramethyl-5,6,7,8-tetrahydro-2-naphthyl)-3-oxopropenyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-hydroxyprop-1-ynyl]benzoic acid, 4-(3-{4-[1-(4-dimethylaminophenyl)-1-methylethoxy]-5,5,8,8-tetramethyl-5,6,7,8-tetrahydro-2-naphthyl}-3-hydroxypropenyl)benzoic acid, 4-(3-{4-[1-(4-dimethylaminophenyl)-1-methylethoxy]-5,5,8,8-tetramethyl-5,6,7,8-tetrahydro-2-naphthyl}-3-oxopropenyl)benzoic acid, 4-(3-{4-[1-(4-dimethylaminophenyl)-1-methylethoxy]-5,5,8,8-tetramethyl-5,6,7,8-tetrahydro-2-naphthyl}-3-hydroxyprop-1-ynyl)benzoic acid, 4-(3-{4-[2-(4-fluorophenyl)ethyl]-5,5,8,8-tetramethyl-5,6,7,8-tetrahydro-2-naphthyl}-3-hydroxypropenyl)benzoic acid, 4-(3-{4-[2-(4-fluorophenyl)ethyl]-5,5,8,8-tetramethyl-5,6,7,8-tetrahydro-2-naphthyl}-3-oxopropenyl)benzoic acid, 4-(3-{4-[2-(4-fluorophenyl)ethyl]-5,5,8,8-tetramethyl-5,6,7,8-tetrahydro-2-naphthyl}-3-hydroxyprop-1-ynyl)benzoic acid, 4-(3-{4-[2-(4-fluorophenyl)-2-methylpropyl]-5,5,8,8-tetramethyl-5,6,7,8-tetrahydro-2-naphthyl}-3-hydroxypropenyl)benzoic acid, 4-(3-{4-[2-(4-fluorophenyl)-2-methylpropyl]-5,5,8,8-tetramethyl-5,6,7,8-tetrahydro-2-naphthyl}-3-oxopropenyl)benzoic acid, 4-(3-{4-[2-(4-fluorophenyl)-2-methylpropyl]-5,5,8,8-tetramethyl-5,6,7,8-tetrahydro-2-naphthyl}-3-hydroxyprop-1-ynyl)benzoic acid, 4-(3-{4-[2-(4-methylphenyl)ethyl]-5,5,8,8-tetramethyl-5,6,7,8-tetrahydro-2-naphthyl}-3-hydroxypropenyl)benzoic acid, 4-(3-{4-[2-(4-methylphenyl)ethyl]-5,5,8,8-tetramethyl-5,6,7,8-tetrahydro-2-naphthyl}-3-oxopropenyl)benzoic acid, 4-(3-{4-[2-(4-methylphenyl)ethyl]-5,5,8,8-tetramethyl-5,6,7,8-tetrahydro-2-naphthyl}-3-hydroxyprop-1-ynyl)benzoic acid, 4-(3-{4-[2-(4-methylphenyl)-2-methylpropyl]-5,5,8,8-tetramethyl-5,6,7,8-tetrahydro-2-naphthyl}-3-hydroxypropenyl)benzoic acid, 4-(3-{4-[2-(4-methylphenyl)-2-methylpropyl]-5,5,8,8-tetramethyl-5,6,7,8-tetrahydro-2-naphthyl}-3-oxopropenyl)benzoic acid, 4-(3-{4-[2-(4-methylphenyl)-2-methylpropyl]-5,5,8,8-tetramethyl-5,6,7,8-tetrahydro-2-naphthyl}3-hydroxyprop-1-ynyl)benzoic acid, 4-(3-{4-[2-(4-dimethylaminophenyl)ethyl]-5,5,8,8-tetramethyl-5,6,7,8-tetrahydro-2-naphthyl}3-hydroxypropenyl)benzoic acid, 4-(3-{4-[2-(4-dimethylaminophenyl)ethyl]-5,5,8,8-tetramethyl-5,6,7,8-tetrahydro-2-naphthyl}-3-oxopropenyl)benzoic acid, 4-(3-{4-[2-(4-dimethylaminophenyl)ethyl]-5,5,8,8-tetramethyl-5,6,7,8-tetrahydro-2-naphthyl}-3-hydroxyprop-1-ynyl)benzoic acid, 4-(3-{4-[2-(4-dimethylaminophenyl)-2-methylpropyl]-5,5,8,8-tetramethyl-5,6,7,8-tetrahydro-2-naphthyl}-3-hydroxypropenyl)benzoic acid, 4-(3-{4-[2-(4-dimethylaminophenyl)-2-methylpropyl]-5,5,8,8-tetramethyl-5,6,7,8-tetrahydro-2-naphthyl}-3-oxopropenyl)benzoic acid, 4-(3-{4-[2-(4-dimethylaminophenyl)-2-methylpropyl]-5,5,8,8-tetramethyl-5,6,7,8-tetrahydro-2-naphthyl}-3-hydroxyprop-1-ynyl)benzoic acid, 4-{3-[4-(4-fluorobenzyloxy)-5,6,7,8-tetrahydro-2-naphthyl]-3-hydroxypropenyl}benzoic acid, 4-{3-[4-(4-fluorobenzyloxy)-8,8-dimethyl-5,6,7,8-tetrahydro-2-naphthyl]-3-hydroxypropenyl}benzoic acid,
4-{3-[4-(4-fluorobenzyloxy)-5,5-dimethyl-5,6,7,8-tetrahydro-2-naphthyl]-3-hydroxypropenyl}benzoic acid,
4-(3-{4-[(4-fluorobenzyl)methylamino]-5,5,8,8-tetramethyl-5,6,7,8-tetrahydro-2-naphthyl}-3-hydroxyprop-1-ynyl)benzamide,
4-(3-{4-[(4-fluorobenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-fluorobenzyl)methylamino]-5,5,8,8-tetramethyl-5,6,7,8-tetrahydro-2-naphthyl}-3-hydroxyprop-1-ynyl)benzamide,
4-{3-[4-(4-fluorobenzyloxy)-5,5,8,8-tetramethyl-5,6,7,8-tetrahydro-2-naphthyl]-3-hydroxyprop-1-ynyl}benzamide,
4-{3-[4-(4-fluorobenzyloxy)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzyloxy)-5,5,8,8-tetramethyl-5,6,7,8-tetrahydro-2-naphthyl]-3-hydroxyprop-1-ynyl}benzamide,
4-{3-[4-(4-fluorobenzylamino)-5,5,8,8-tetramethyl-5,6,7,8-tetrahydro-2-naphthyl]-3-hydroxyprop-1-ynyl}benzamide,
4-{3-[4-(4-fluorobenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzylamino)-5,5,8,8-tetramethyl-5,6,7,8-tetrahydro-2-naphthyl]-3-hydroxyprop-1-ynyl}benzamide,
4-{3-[4-(4-fluorobenzylsulfanyl)-5,5,8,8-tetramethyl-5,6,7,8-tetrahydro-2-naphthyl]-3-hydroxyprop-1-ynyl}benzamide,
4-(3-(4-(4-fluorobenzylsulfanyl)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzylsulfanyl)-5,5,8,8-tetramethyl-5,6,7,8-tetrahydro-2-naphthyl]-3-hydroxyprop-1-ynyl}benzamide,
N-ethyl-4-(3-{4-[(4-fluorobenzyl)methylamino]-5,5,8,8-tetramethyl-5,6,7,8-tetrahydro-2-naphthyl}-3-hydroxyprop-1-ynyl)-N-methylbenzamide,
N-ethyl-4-{3-[4-(4-fluorobenzyloxy)-5,5,8,8-tetramethyl-5,6,7,8-tetrahydro-2-naphthyl]-3-hydroxyprop-1-ynyl}-N-methylbenzamide,
N-ethyl-4-{3-[4-(4-fluorobenzylamino)-5,5,8,8-tetramethyl-5,6,7,8-tetrahydro-2-naphthyl]-3-hydroxyprop-1-ynyl}-N-methylbenzamide,
N-ethyl-4-{3-[4-(4-fluorobenzylsulfanyl)-5,5,8,8-tetramethyl-5,6,7,8-tetrahydro-2-naphthyl]-3-hydroxyprop-1-ynyl}-N-methylbenzamide,
4-(3-{4-[(4-methylbenzyl)methylamino]-5,5,8,8-tetramethyl-5,6,7,8-tetrahydro-2-naphthyl}-3-hydroxyprop-1-ynyl)benzamide,
4-(3-{4-[(4-methylbenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-methylbenzyl)methylamino]-5,5,8,8-tetramethyl-5,6,7,8-tetrahydro-2-naphthyl}-3-hydroxyprop-1-ynyl)benzamide,
4-{3-[4-(4-methylbenzyloxy)-5,5,8,8-tetramethyl-5,6,7,8-tetrahydro-2-naphthyl]-3-hydroxyprop-1-ynyl}benzamide,
4-{3-[4-(4-methylbenzyloxy)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzyloxy)-5,5,8,8-tetramethyl-5,6,7,8-tetrahydro-2-naphthyl]-3-hydroxyprop-1-ynyl}benzamide,
4-{3-[4-(4-methylbenzylamino)-5,5,8,8-tetramethyl-5,6,7,8-tetrahydro-2-naphthyl]-3-hydroxyprop-1-ynyl}benzamide,
4-{3-[4-(4-methylbenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzylamino)-5,5,8,8-tetramethyl-5,6,7,8-tetrahydro-2-naphthyl]-3-hydroxyprop-1-ynyl}benzamide,
4-{3-[4-(4-methylbenzylsulfanyl)-5,5,8,8-tetramethyl-5,6,7,8-tetrahydro-2-naphthyl]-3-hydroxyprop-1-ynyl}benzamide,
4-{3-[4-(4-methylbenzylsulfanyl)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzylsulfanyl)-5,5,8,8-tetramethyl-5,6,7,8-tetrahydro-2-naphthyl]-3-hydroxyprop-1-ynyl}benzamide,
N-ethyl-4-(3-{4-[(4-methylbenzyl)methylamino]-5,5,8,8-tetramethyl-5,6,7,8-tetrahydro-2-naphthyl}-3-hydroxyprop-1-ynyl)-N-methylbenzamide,
N-ethyl-4-{3-[4-(4-methylbenzyloxy)-5,5,8,8-tetramethyl-5,6,7,8-tetrahydro-2-naphthyl]-3-hydroxyprop-1-ynyl}-N-methylbenzamide,
N-ethyl-4-{3-[4-(4-methylbenzylamino)-5,5,8,8-tetramethyl-5,6,7,8-tetrahydro-2-naphthyl]-3-hydroxyprop-1-ynyl}-N-methylbenzamide,
N-ethyl-4-{3-[4-(4-methylbenzylsulfanyl)-5,5,8,8-tetramethyl-5,6,7,8-tetrahydro-2-naphthyl]-3-hydroxyprop-1-ynyl}-N-methylbenzamide,
4-(3-{4-[(4-dimethylaminobenzyl)methylamino]-5,5,8,8-tetramethyl-5,6,7,8-tetrahydro-2-naphthyl}-3-hydroxyprop-1-ynyl]benzamide,
4-(3-{4-[(4-dimethylaminobenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-dimethylaminobenzyl)methylamino]-5,5,8,8-tetramethyl-5,6,7,8-tetrahydro-2-naphthyl}3-hydroxyprop-1-ynyl)benzamide,
4-{3-[4-(4-dimethylaminobenzyloxy)-5,5,8,8-tetramethyl-5,6,7,8-tetrahydro-2-naphthyl]-3-hydroxyprop-1-ynyl}benzamide,
4-{3-[4-(4-dimethylaminobenzyloxy)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-dimethylaminobenzyloxy)-5,5,8,8-tetramethyl-5,6,7,8-tetrahydro-2-naphthyl]-3-hydroxyprop-1-ynyl}benzamide,
4-{3-[4-(4-dimethylaminobenzylamino)-5,5,8,8-tetramethyl-5,6,7,8-tetrahydro-2-naphthyl]-3-hydroxyprop-1-ynyl}benzamide,
4-{3-[4-(4-dimethylaminobenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-dimethylaminobenzylamino)-5,5,8,8-tetramethyl-5,6,7,8-tetrahydro-2-naphthyl]-3-hydroxyprop-1-ynyl}benzamide,
4-{3-[4-(4-dimethylaminobenzylsulfanyl)-5,5,8,8-tetramethyl-5,6,7,8-tetrahydro-2-naphthyl]-3-hydroxyprop-1-ynyl}benzamide,
4-{3-[4-(4-dimethylaminobenzylsulfanyl)-5,5,8,8-tetramethyl-5,6,7,8-tetrahydro-2-naphthyl]-3-hydroxyprop-1-ynyl}-N-hydroxybenzamide, N-ethyl-4-{3-[4-(4-dimethylaminobenzylsulfanyl)-5,5,8,8-tetramethyl-5,6,7,8-tetrahydro-2-naphthyl]-3-hydroxyprop-1-ynyl}benzamide, N-ethyl-4-(3-{4-[(4-dimethylaminobenzyl)methylamino]-5,5,8,8-tetramethyl-5,6,7,8-tetrahydro-2-naphthyl]-3-hydroxyprop-1-ynyl)-N-methylbenzamide, N-ethyl-4-{3-[4-(4-dimethylaminobenzyloxy)-5,5,8,8-tetramethyl-5,6,7,8-tetrahydro-2-naphthyl]-3-hydroxyprop-1-ynyl}-N-methylbenzamide, N-ethyl-4-{3-[4-(4-dimethylaminobenzylamino)-5,5,8,8-tetramethyl-5,6,7,8-tetrahydro-2-naphthyl]-3-hydroxyprop-1-ynyl}-N-methylbenzamide and N-ethyl-4-{3-[4-(4-dimethylaminobenzylsulfanyl)-5,5,8,8-tetramethyl-5,6,7,8-tetrahydro-2-naphthyl]-3-hydroxyprop-1-ynyl}-N-methylbenzamide.

According to the present invention, the compounds of formula (I) that are more particularly preferred are those in which:

$R_1$ is (b),
Q is an oxygen atom, and
$R_9$ is (i).

The present invention also features the processes for preparing the compounds of formula (I), in particular according to the reaction schemes shown in the FIGURE of Drawing.

A general description of the preparation of the compounds of general formulae 6 to 12 is given below.

Intermediate 2 may be formed from 3-bromophenol, via a Friedel-Crafts reaction in the presence of aluminum chloride and a corresponding partner, for instance 2,5-dichloro-2,5-dimethylhexane. The compounds of general structure 3 may be obtained by converting the bromide of 2 into an acid or an aldehyde after lithiation with butyllithium, or, in the case where R=SH or SeH, the compounds of general structure 3 may be obtained by lithiation of 3 and attack of the anion formed on the native sulfur or selenium.

These compounds may then be converted into the corresponding disulfides or diselenides by spontaneous oxidation in non-gassed ethanol, after which the compounds 4 may be prepared by forming the sulfide or selenide bromide by the action of bromine on the disulfide or diselenide function, followed by addition of a true alkyne in the presence of copper iodide in dimethylformamide, for example. After O-alkylation of the phenol function of the compounds of structure 4, for example by nucleophilic substitution with a halogenated compound in the presence of sodium hydride, the compounds of structure 6 are obtained after saponification of the ester function, for example by reaction with sodium hydroxide.

In the case where Q=O, the compounds 5 may be obtained after O-alkylation of the phenol function of the compounds of structure 3, for example by nucleophilic substitution with a halogenated compound in the presence of sodium hydride. In the case where Q=S or N—R, the phenol may first be converted into trifluoromethanesulfonyl by reaction with trifluoromethanesulfonic anhydride, and this intermediate is then coupled with a thiolate or an amine, respectively, in the presence of transition metal complexes, for instance bis-pyridyidichloronickel or dichlorobisphosphinoferrocenylpalladium, respectively. In the case where Q=$CR_{11}R_{12}$ or C=O, the compound obtained after reaction of 3 with trifluoromethanesulfonic anhydride may be coupled according to the Stille procedure with, for example, organotin derivatives, with or without pressure of carbon monoxide, respectively.

The compounds 3 for which R=COOR' may be converted into acids by saponification, and then into methyl ketones by reaction with methyl lithium: the compounds 5 in which R=COMe will thus be obtained.

When the compounds of general structure 5 are obtained, compounds 7-12 are obtained in the following manner:

The compounds 7 may be obtained by forming the acids corresponding to the esters 5, followed by conversion of these acids into the acid chlorides thereof, for example by reaction with thionyl chloride. These acid chlorides may then be coupled with organometallic derivatives of naphthylzinc type, or with naphthoic boronic acids, in the presence of catalysts based on transition metals, for example tetrakis (triphenylphosphino)palladium. The precursors of the compounds of general structure 7 are generally obtained in the form of esters: the acids of structure 7 may be obtained by saponification, for example by reaction with sodium hydroxide.

The compounds 8 may be prepared by forming a chalcone bond by reacting the methyl ketone of 5 with a corresponding aromatic aldehyde in the presence of potassium hydroxide.

The compounds of general structure 9 may be prepared from the aldehyde 5 by creating a propargyl alcohol function by addition of a propargyl anion, for example by reaction with ethynyl magnesium bromide, followed by a Sonogashira coupling with an aromatic halide, for instance 4-iodobenzoic acid in the presence of copper salts and a catalyst based on a transition metal complex, for instance tetrakis (triphenylphosphino)palladium.

The compounds of general structure 10 may be obtained from the compounds of structure 7, for example after reduction or alkylation of the carbonyl function (R,R'=OH, H or alkyl, respectively), or alternatively by reduction followed by a dehydroxylation (R,R'=H, H), or acetalization of the carbonyl function (R,R'=OR, OR), or formation of an oxime on the carbonyl function of 7 by reaction with a corresponding hydroxyl or alkoxylamine.

The compounds of general structure 11 may be obtained from the compounds of structure 8, for example after reduction or alkylation of the carbonyl function (R,R'=OH, H or alkyl, respectively), for example by reaction with sodium borohydride or an alkymagnesium halide.

The compounds of general structure 12 may be prepared from the compounds of structure 9, by oxidation of the benzyl alcohol to a ketone (R,R'=C=O), for example after reaction with manganese oxide, or oxidation followed by the formation of an oxime on the carbonyl function of 9 by reaction with a corresponding hydroxyl or alkoxylamine (R,R'=C=N—OR), or dehydroxylation of the benzyl alcohol function (R,R'=H, H), for example by reaction with triethylsilane in the presence of boron trifluoride, or by oxidation and formation of an acetal (R,R'=OR, OR), or by oxidation and alkylation of the carbonyl function (R,R'=alkyl, OH), for example by addition of an alkylmagnesium halide, or by O-alkylation of the alcohol function of 9 (R,R'=OR, H).

The compounds according to the invention have inhibitory properties of RAR-type receptors. This RAR-receptor inhibitory activity is measured in a test of transactivation by means of the dissociation constant Kdapp (apparent) and the $IC_{50}$ (concentration that inhibits 50% of the reference agonist activity).

According to the invention, the expression "inhibitor of RAR-type receptors" means any compound which, for at least one of the RAR subtypes, has a dissociation constant Kdapp of less than or equal to 1 μm, and an $IC_{50}$ value ≤100 nM, in a transactivation test as described in Example 19 below.

The preferred compounds of the present invention have, for at least one of the RAR subtypes, a dissociation constant Kdapp of less than or equal to 500 nM and advantageously less than or equal to 100 Nm, and an $IC_{50} \leq 25$ nM.

The present invention also features administration of the compounds of formula (I) as described above, as medicinal/therapeutic products.

The compounds according to the invention are particularly suitable in the following regimes or regimens of treatment:

1) for treating dermatological conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;
2) for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;
3) for treating other dermatological conditions or afflictions having an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;
4) for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any cutaneous precancerous lesion such as keratoacanthomas;
5) for treating other dermatological disorders such as immune dermatoses, such as lupus erythematosus, immune bullous diseases and collagen diseases, such as scleroderma;
6) for the treatment of dermatological or general conditions or afflictions having an immunological component;
7) for treating certain ophthalmological disorders, especially corneopathies,
8) for preventing or curing the stigmata of epidermal and/or dermal atrophy induced by local or systemic corticosteroids, or any other form of cutaneous atropy,
9) for the treatment of any cutaneous or general conditions or afflictions of viral origin,
10) for the treatment of skin disorders caused by exposure to UV radiation, and also for repairing or combating aging of the skin, whether photoinduced or chronological aging, or for reducing pigmentations and actinic keratosis, or any pathology associated with chronological or actinic aging, such as xerosis;
11) for combating sebaceous function disorders, such as the hyperseborrhoea of acne or simple seborrhoea;
12) for preventing or treating cicatrization disorders, or for preventing or repairing stretch marks, or alternatively for promoting cicatrization;
13) for the treatment of pigmentation disorders, such as hyperpigmentation, melasma, hypopigmentation or vitiligo;
14) for the treatment of lipid metabolism conditions or afflictions, such as obesity, hyperlipidaemia, or non-insulin-dependent diabetes;
15) for the treatment of inflammatory conditions or afflictions such as arthritis;
16) for the treatment or prevention of cancerous or precancerous conditions;
17) for the prevention or treatment of alopecia of various origins, especially alopecia caused by chemotherapy or radiation;
18) for the treatment of disorders of the immune system, such as asthma, type I sugar diabetes, multiple sclerosis or other selective dysfunctions of the immune system; and
19) for the treatment of conditions or afflictions of the cardiovascular system, such as arteriosclerosis or hypertension.

The present invention also features pharmaceutical compositions comprising, formulated into a physiologically acceptable medium, at least one compound of formula (I) as defined above.

This invention also features novel medicinal compositions suited for treating the abovementioned conditions, disorders or afflictions which are characterized in that they comprise, formulated into a pharmaceutically acceptable support that is compatible with the mode of administration selected for the composition, at least one compound of formula (I), an optical isomer thereof or a salt thereof.

The compositions according to the invention may be administered enterally, parenterally, topically or ocularly. The pharmaceutical composition is preferably packaged in a form that is suitable for topical application.

Via the enteral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered at a daily dose of about 0.01 mg/kg to 100 mg/kg of body weight, in 1 to 3 dosage intakes.

The compounds are administered systemically, at a concentration generally ranging from 0.001% to 10% by weight and preferably from 0.01% to 1% by weight relative to the weight of the composition.

Via the topical route, the pharmaceutical compositions according to the invention are more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. There may also be in the form of suspensions of microspheres or nanospheres or of lipid or polymer vesicles or gelled or polymer patches allowing a controlled release.

The compounds are administered topically at a concentration generally ranging from 0.001% to 10% by weight and from 0.01% to 1% by weight, relative to the total weight of the composition.

The compounds of formula (I) according to the invention also find applications in cosmetics, in particular in body and hair hygiene and especially for treating acne-prone skin, for promoting regrowth of the hair or for limiting hair loss, for combating the greasy appearance of the skin or the hair, for protection against the harmful aspects of sunlight or for the treatment of physiologically dry skin, and for preventing and/or combating photoinduced or chronological aging.

This invention thus also features compositions comprising, formulated into a cosmetically acceptable support, at least one of the compounds of formula (I).

The present invention also features the cosmetic use of compositions comprising at least one compound of formula (I) for preventing and/or treating the signs of aging and/or dry skin.

This invention also features the cosmetic use of a composition comprising at least one compound of formula (I) for body or hair hygiene.

The cosmetic compositions according to the invention containing, formulated into a cosmetically acceptable support, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, shampoos or washing bases.

The concentration of compound of formula (I) in the cosmetic composition preferably ranges from 0.001% to 3% by weight relative to the total weight of the composition.

The pharmaceutical and cosmetic compositions as described above may also contain inert additives, or even pharmacodynamically active additives as regards the pharmaceutical compositions, or combinations of these additives, and especially:

wetting agents;
flavor enhancers;
preservatives such as para-hydroxybenzoic acid esters;
stabilizers;
moisture regulators;
pH regulators;
osmotic pressure modifiers;
emulsifiers;
UV-A and UV-B screening agents;
antioxidants such as α-tocopherol, butylhydroxyanisole, butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and its derivatives or urea;
antiseborrhoeic or antiacne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclines;
antifungal agents such as ketoconazole or poly-4,5-methylene-3-isothiazolidones;
agents for promoting regrowth of the hair, for instance Minoxidil (2,4-diamino-6-piperidinopyrimidine 3-oxide) and its derivatives, Diazoxide (7-chloro 3-methyl-1,2,4-benzothiadiazine 1,1-dioxide) and Phenyloin (5,4-diphenylimidazolidine-2,4-dione);
non-steroidal anti-inflammatory agents;
carotenoids and especially α-carotene;
anti-psoriatic agents such as anthralin and its derivatives;
eicosa-5,8,11,14-tetraynoic acid and eicosa-5,8,11-triynoic acid, and esters and amides thereof;
retinoids, i.e., natural or synthetic RXR receptor ligands;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;
ion-channel blockers such as potassium-channel blockers;
or alternatively, more particularly for pharmaceutical compositions, in combination with medicinal active agents known to interfere with the immune system (for example cyclosporin, FK 506, glucocorticoids, monoclonal antibodies, cytokines or growth factors, etc.).

Needless to say, one skilled in the art will take care to select the optional compound(s) to be added to these compositions such that the advantageous properties intrinsically associated with the present invention are not, or are not substantially, adversely affected by the envisaged addition.

Several examples of the production of active compounds of formula (I) according to the invention, biological activity results and also various concrete formulations based on such compounds, will now be given, for illustrative purposes and in nowise limitative. In said examples to follow, all parts and percentages are given by weight, unless otherwise indicated.

EXAMPLE 1

Synthesis of 4-[4-(3-fluorobenzyloxy)-5,5,8,8-tetramethyl-5,6,7,8-tetrahydro-2-naphthylselanylethynyl]benzoic acid a. Preparation of 3-Bromo-5,5,8,8-tetramethyl-5,6,7,8-tetrahydro-1-naphthyl:

60 g (347 mmol) of 3-bromophenol are dissolved in 600 mL of dichloromethane. This solution is added to a solution of 46 g (347 mmol) of aluminum chloride in 200 mL of dichloromethane. 127 g (694 mmol) of 2,5-dichloro-2,5-dimethylhexane are added in 10 g portions every 40 minutes. The medium is then stirred for 10 hours, after which it is poured onto ice and extracted with dichloromethane. The residue obtained is dissolved in ethyl ether and this organic phase is then washed with 1 N sodium hydroxide solution and then with water. The residue obtained is purified by chromatography (eluent: heptane and then 1/1 heptane/dichloromethane). A thick oil is obtained (67 g; yield=68%).

b. Preparation of 7-Bromo-5-ethoxymethoxy-1,1,4,4-tetramethyl-1,2,3,4-tetrahydronaphthalene:

42 g (148 mmol) of 3-bromo-5,5,8,8-tetramethyl-5,6,7,8-tetrahydro-1-naphthyl are dissolved in 400 mL of anhydrous DMF. 7.2 g (178 mmol) of 60% sodium hydride are added portionwise and the reaction medium is stirred for one hour. 16.5 mL (178 mmol) of ethoxymethyl chloride are added dropwise and the medium is stirred at room temperature for 2 hours and then hydrolyzed and extracted with ethyl ether. The organic phase is washed with 1 N sodium hydroxide solution and then three times with water. The residue obtained is purified by chromatography (eluent:heptane). A yellow oil is obtained (m=45.7 g; yield=95%).

c. Preparation of Bis(4-ethoxymethoxy-5,5,8,8-tetramethyl-5,6,7,8-tetrahydro-2-naphthalene)diselenide:

10 g (30.8 mmol) of 7-bromo-5-ethoxymethoxy-1,1,4,4-tetramethyl-1,2,3,4-tetrahydronaphthalene are dissolved in 200 mL of anhydrous THF. The medium is cooled to −78° C. and 20 mL (34 mmol) of 1.7 M tert-butyllithium solution are added dropwise. The medium is stirred for one hour and then added via a cannula to a suspension of 2.68 g (34 mmol) of selenium in 100 mL [lacuna] at −78° C. The reaction medium is warmed to room temperature and then stirred for 2 hours and treated with saturated ammonium chloride solution. The residue obtained after extraction is dissolved in 100 mL of ethanol, and 100 mg of sodium hydroxide are added. The reaction medium is stirred for 12 hours and then concentrated. The desired product is obtained after purification by chromatography (eluent: 95/5 heptane/ethyl acetate) (m=10 g, yield=95%).

d. Preparation of Methyl 4-(4-ethoxymethoxy-5,5,8,8-tetramethyl-5,6,7,8-tetrahydro-2-naphthylselanylethynyl)benzoate:

10 g (14.7 mmol) of bis(4-ethoxymethoxy-5,5,8,8-tetramethyl-5,6,7,8-tetrahydro-2-naphthalene) diselenide are dissolved in 200 mL of anhydrous THF and the medium is cooled to −78° C. 13.9 mL (13.9 mmol) of a 1 N solution of bromine in THF are added slowly. The medium is stirred for one hour and 300 mL of DMF are then added, followed by addition of 4.65 g (26.4 mmol) of methyl 4-ethynylbenzoate and 16.8 g of copper iodide. The reaction medium is warmed to room temperature and stirred for 48 hours, and is then hydrolyzed and extracted with ethyl acetate. A thick oil is obtained after purification by chromatography (eluent: 9/1 heptane/ethyl acetate) (m=9.8 g; yield=74%).

e. Preparation of Methyl 4-(4-hydroxy-5,5,8,8-tetramethyl-5,6,7,8-tetrahydro-2-naphthylselanylethynyl]benzoate:

9 g (18 mmol) of methyl 4-(4-ethoxymethoxy-5,5,8,8-tetramethyl-5,6,7,8-tetrahydro-2-naphthylselanyethynyl)benzoate are dissolved in 100 mL of methanol, and 2 mL of sulfuric acid are added. The medium is refluxed for 2 hours and is then hydrolyzed and extracted with dichloromethane. The residue is purified by chromatography (eluent: dichloromethane). A yellow solid is obtained (m=7.2 g; yield=90%; m.p.=139° C.).

f. Preparation of Methyl 4-[4-(3-fluorobenzyloxy)-5,5,8,8-tetramethyl-5,6,7,8-tetrahydro-2-naphthylselanylethynyl]benzoate:

600 mg (1.35 mmol) of methyl 4-(4-hydroxy-5,5,8,8-tetramethyl-5,6,7,8-tetrahydro-2-naphthylselanylethynyl]benzoate are dissolved in 40 mL of 2-butanone. 182 µl (1.48 mmol) of 3-fluorobenzyl bromide are added, followed by addition of 250 mg (1.8 mmol) of potassium carbonate. The reaction medium is refluxed for 10 ten hours and then cooled and filtered. After washing the solid residue obtained with heptane, a white solid is obtained (m=683 mg; yield=92%; m.p.=132° C.).

g. Synthesis of 4-[4-(3-fluorobenzyloxy)-5,5,8,8-tetramethyl-5,6,7,8-tetrahydro-2-naphthylselanlethynyl]benzoic acid:

650 mg (1.2 mmol) of methyl 4-[4-(3-fluorobenzyloxy)-5,5,8,8-tetramethyl-5,6,7,8-tetrahydro-2-naphthylselanylethynyl]benzoate are dissolved in 20 mL of THF. 10 mL of water are added, followed by addition of 240 mg (6 mmol) of sodium hydroxide. The medium is stirred for 4 hours at 80° C. and then acidified with 1 N hydrochloric acid and extracted with ethyl acetate. The residue obtained is purified by chromatography (eluent: 1/1 heptane/ethyl acetate) and then recrystallized in a heptane/ethyl acetate mixture. A pure yellow crystalline solid is obtained (m=577 mg; yield=90%; m.p.=206° C.

$^1$H NMR (DMSO): 1.31 (S, 6H); 1.40 (S, 6H); 1.63-1.68 (m, 4H); 5.24 (s, 2H); 7.17 (s, 1H): 7.22 (m, 1H); 7.32-7.37 (m, 3H); 7.48 (m, 11H); 7.63 (d, J=8.2 Hz, 2H); 8.01 (d, J=8.2 Hz, 2H); 13.1 (bs, 1H).

EXAMPLE 2

Synthesis of 4-[5,5,8,8-tetramethyl-4-(4-methylbenzyloxy)-5,6,7,8-tetrahydro-2-naphthylselanylethynyl]benzoic acid a. Preparation of Methyl 4-[5,5,8,8-tetramethyl-4-(4-methylbenzyloxy)-5,6,7,8-tetrahydro-2-naphthylselanylethynyl]benzoate:

In a manner similar to that of Example 1f, by reacting 600 mg (1.35 mmol) of methyl 4-(4-hydroxy-5,5,8,8-tetramethyl-5,6,7,8-tetrahydro-2-naphthylselanylethynyl)benzoate with 250 mg (1.8 mmol) of potassium carbonate and 274 µL (1.5 mmol) of 4-methylbenzyl bromide. A white solid is obtained (m=708 mg; yield=96%; m.p.=154° C.).

b. Synthesis of 4-[5,5,8,8-tetramethyl-4-(4-methylbenzyloxy)-5,6,7,8-tetrahydro-2-naphthylselanylethynyl]benzoic acid:

In a manner similar to Example 1g, by reacting 650 mg (1.2 mmol) of methyl 4-[5,5,8,8-tetramethyl-4-(4-methylbenzyloxy)-5,6,7,8-tetrahydro-2-naphthylselanylethynyl] benzoate with 240 mg of sodium hydroxide. A yellow crystallized solid is obtained (m=580 mg; yield=91%; m.p.=254° C.).

$^1$H NMR (CDCl$_3$+DMSO): 1.29 (s, 6H); 1.37 (s, 6H); 1.61-1.64 (m, 4H); 2.40 (s, 3H); 5.04 (s, 2H); 7.0 (s, 1H): 7.16 (m, 3H); 7.17 (m, 2H); 7.45 (d, J=6.8 Hz, 2H); 8.00 (d, J=6.8 Hz, 2H)

EXAMPLE 3

Synthesis of 4-[4-(4-tert-butylbenzyloxy)-5,5,8,8-tetramethyl-5,6,7,8-tetrahydro-2-naphthylselanylethynyl]benzoic acid a. Preparation of Methyl 4-[5,5,8,8-tetramethyl-4-(4-tert-butylbenzyloxy)-5,6,7,8-tetrahydro-2-naphthylselanylethynyl]benzoate:

In a manner similar to that of Example 1f, by reacting 600 mg (1.38 mmol) of methyl 4-(4-hydroxy-5,5,8,8-tetramethyl-5,6,7,8-tetrahydro-2-naphthylselanylethynyl)benzoate with 240 mg (1.6 mmol) of potassium carbonate and 300 µL (1.6 mmol) of 4-tert-butylbenzyl bromide. A white solid is obtained (m=640 mg; yield=80%; m.p.=138° C.).

b. Synthesis of 4-[5,5,8,8-tetramethyl-4-(4-tert-butylbenzyloxy)-5,6,7,8-tetrahydro-2-naphthylselanylethynyl]benzoic acid:

In a manner similar to that of Example 1g, by reacting 640 mg (1.2 mmol) of methyl 4-[5,5,8,8-tetramethyl-4-(4-tert-butylbenzyloxy)-5,6,7,8-tetrahydro-2-napthylselanylethynyl]benzoate with 240 mg of sodium hydroxide. A yellow crystallized solid is obtained (m=530 mg; yield=92%; m.p.=285° C.).

$^1$H NMR (CDCl$_3$)1.24 (s, 6H); 1.35 (s, 9H); 1.42 (s, 6H); 1.66 (m, 4H); 5.09 (s. 2H); 7.04 (d, 1H, 1.6 Hz); 7.22 (d, 1H, 1.6 Hz); 7.40 (dd, 4H, J1=4 Hz, J2=13 Hz); 7.52 (d, 2H, 8 Hz); 8.06 (d, 2H, 8 Hz).

EXAMPLE 4

Synthesis of 4-[4-(3,4-difluorobenzyloxy)-5,5,8,8-tetramethyl-5,6,7,8-tetrahydro-2-naphthylselanylethynyl]benzoic acid a. Preparation of Methyl 4-[5,5,8,8-tetramethyl-4-(3,4-difluorobenzyloxy)-5,6,7,8-tetrahydro-2-naphthylselanylethynyl]benzoate:

In a manner similar to Example 1f, by reacting 600 mg (1.38 mmol) of methyl 4-(4-hydroxy-5,5,8,8-tetramethyl-5,6,7,8-tetrahydro-2-naphthylselanylethynyl]benzoate with 240 mg (1.6 mmol) of potassium carbonate and 210 µL (1.6 mmol) of 3,4-difluorobenzyl bromide. A white solid is obtained (m=680 mg; yield=86%; m.p.=118° C.).

b. Synthesis of 4-[5,5,8,8-tetramethyl-4-(3,4-difluorobenzyloxy)-5,6,7,8-tetrahydro-2-naphthylselanylethynyl]benzoic acid:

In a manner similar to Example 1g, by reacting 680 mg (1.2 mmol) of methyl 4-[5,5,8,8-tetramethyl-4-(3,4- difluorobenzyloxy)-5,6,7,8-tetrahydro-2-naphthylselanyl-ethynyl]benzoate with 240 mg of sodium hydroxide. A yellow crystallized solid is obtained (m=402 mg; yield=61%; m.p.=218° C.).

$^1$H NMR (CDCl$_3$) 1.32 (s, 6H); 1.39 (s, 6H); 1.66 (m, 4H); 5.06 (s, 2H); 6.94 (d, 1H, 4 Hz); 7.14 (m, 2H); 7.23 (m, 1H); 7.28 (d, 1H, 4 Hz); 7.51 (d, 2H, 5, 6 Hz); 8.07 (d, 2H, 4 Hz).

EXAMPLE 5

Synthesis of 4-[4-(2,4-difluorobenzyloxy)-5,5,8,8-tetramethyl-5,6,7,8-tetrahydro-2-naphthylselanyl-ethynyl]benzoic acid a. Preparation of Methyl 4-(5,5,8,8-tetramethyl-4-(2,4-difluorobenzyloxy)-5,6,7,8-tetrahydro-2-naphthylselanyl-ethynyl]benzoic acid:

In a manner similar to that of Example 1f, by reacting 600 mg (1.38 mmol) of methyl 4-(4-hydroxy-5,5,8,8-tetramethyl-5,6,7,8-tetrahydro-2-naphthylselanylethynyl]benzoic acid with 240 mg (1.6 mmol) of potassium carbonate and 200 μL (1.7 mmol) of 2,4-difluorobenzyl bromide. A white solid is obtained (m=790 mg; yield=100%; m.p.=115° C.).

b. Synthesis of 4-[5,5,8,8-tetramethyl-4-(2,4-difluorobenzyloxy)-5,6,7,8-tetrahydro-2-naphthylselanylethynyl]benzoic acid:

In a manner similar to that of Example 1g, by reacting 790 mg (1.4 mmol) of methyl 4-[5,5,8,8-tetramethyl-4-(2,4-difluorobenzyloxy)-5,6,7,8-tetrahydro-2-naphthylselanyl-ethynyl]benzoate with 240 mg of sodium hydroxide. A yellow crystallized solid is obtained (m=502 mg; yield=65%; m.p.=219° C.).

$^1$H NMR (CDCl$_3$)1.31 (s, 6H); 1.37 (s, 6H); 1.65 (m, 4H); 5.12 (s, 2H); 6.90 (m, 2H); 7.03 (d, 1H, 1.6 Hz); 7.22 (d, 1H, 2 Hz); 7.51 (m, 3H); 8.08 (d, 2H, 8 Hz).

EXAMPLE 6

Synthesis of 4-[4-(4-trifluoromethylbenzyloxy)-(5,5,8,8-tetramethyl-5,6,7,8-tetrahydro-2-naphthylsela-nylethynyl]benzoic acid a. Preparation of Methyl 4-[5,5,8,8-tetramethyl-4-(4-trifluoromethylbenzyloxy)-5,6,7,8-tetrahydro-2-naphthylsela-nylethynyl]benzoate:

In a manner similar to that of Example 1f, by reacting 590 mg (1.3 mmol) of methyl 4-(4-hydroxy-5,5,8,8-tetramethyl-5,6,7,8-tetrahydro-2-naphthylselanylethynyl]benzoate with 240 mg (1.6 mmol) of potassium carbonate and 383 mg (1.6 mmol) of 4-trifluoromethylbenzyl bromide. A white solid is obtained (m=840 mg; yield=100%; m.p.=156° C.).

b. Synthesis of 4-[5,5,8,8-tetramethyl-4-(4-trifluorometh-ylbenzyloxy)-5,6,7,8-tetrahydro-2-naphthylselanylethynyl] benzoic acid:

In a manner similar to that of Example 1g, by reacting 840 mg (1.4 mmol) of methyl 4-[5,5,8,8-tetramethyl-4-(4-trif-luoromethylbenzyloxy)-5,6,7,8-tetrahydro-2-naphthylsela-nylethynyl]benzoate with 240 mg of sodium hydroxide. A white crystallized solid is obtained (m=614 mg; yield=72%; m.p.=253° C.).

$^1$H NMR (DMSO) 1.17 (s, 6H); 1.34 (s, 6H); 1.59 (m, 4H); 5.27 (s, 2H); 7.11 (d, 1H, 4 Hz); 7.27 (d, 1H, 4 Hz); 7.55 (d, 2H, 8 Hz); 7.67 (d, 2H, 8 Hz); 7.73 (d, 2H, 8 Hz); 7.94 (d, 2H, 8 Hz); 13.10 (s, 1H).

EXAMPLE 7

Synthesis of 4-[5,5,8,8-tetramethyl-4-(naphthyl-methoxy)-5,6,7,8-tetrahydro-2-naphthylselanylethy-nyl]benzoic acid a. Preparation of Methyl-4-[5,5,8,8-tetramethyl-4-(naph-thylmethoxy)-5,6,7,8-tetrahydro-2-naphthylselanylethynyl] benzoate:

In a manner similar to that of Example 1f, by reacting 368 mg (0.8 mmol) of methyl 4-(4-hydroxy-5,5,8,8-tetramethyl-5,6,7,8-tetrahydro-2-naphthylselanylethynyl]benzoate with 140 mg (1 mmol) of potassium carbonate and 221 mg (1 mmol) of 2-bromomethylnaphthalene. A white solid is obtained (m=400 mg; yield=83%; m.p.=134° C.).

b. Synthesis of 4-[5,5,8,8-tetramethyl-4-(naphthyl-methoxy)-5,6,7,8-tetrahydro-2-naphthylselanylethynyl]ben-zoic acid:

In a manner similar to that of Example 1g, by reacting 400 mg (0.7 mmol) of methyl 4-[5,5,8,8-tetramethyl-4-(naphth-ylmethoxy)-5,6,7,8-tetrahydro-2-naphthylselanylethynyl] benzoate with 140 mg of sodium hydroxide. A white crystallized solid is obtained (m=258 mg; yield=65%; m.p.=254° C.).

$^1$H NMR (DMSO) 1.25 (s, 6H); 1.35 (s, 6H); 1.58 (m, 4H); 5.31 (s, 2H); 7.19 (d, 1H, 1.6 Hz); 7.26 (d, 1H, 1.6 Hz); 7.53 (m, 4H); 7.59 (d, 1H, 8 Hz); 7.85 (m, 1H); 7.96 (m, 4H); 7.98 (s, 1H).

EXAMPLE 8

Synthesis of 4-[4-(4-chlorobenzyloxy)-5,5,8,8-tet-ramethyl-5,6,7,8-tetrahydro-2-naphthylselanylethy-nyl]benzoic acid a. Preparation of Methyl 4-[5,5,8,8-tetramethyl-4-(4-chlorobenzyloxy)-5,6,7,8-tetrahydro-2-naphthylselanyl-ethynyl]benzoate:

In a manner similar to that of Example 1f, by reacting 370 mg (0.8 mmol) of methyl 4-(4-hydroxy-5,5,8,8-tetramethyl-5,6,7,8-tetrahydro-2-naphthylselanylethynyl]benzoate with 140 mg (1 mmol)of potassium carbonate and 205 mg (1 mmol) of 4-chlorobenzyl bromide. A white solid is obtained (m=300 mg; yield=64%).

b. Synthesis of 4-[5,5,8,8-tetramethyl-4-(4-chlorobenzy-loxy)-5,6,7,8-tetrahydro-2-naphthylselanylethynyl]benzoic acid:

In a manner similar to that of Example 1g, by reacting 300 mg (0.5 mmol) of methyl 4-[5,5,8,8-tetramethyl-4-(4-chlo-robenzyloxy)-5,6,7,8-tetrahydro-2-naphthylselanylethynyl] benzoate with 110 mg of sodium hydroxide. A white crys-tallized solid is obtained (m=210 mg; yield=72%, m.p.=255° C.).

$^1$H NMR (DMSO) 1.24 (s, 6H); 1.32 (s, 6H); 1.59 (m, 4H); 5.15 (s, 2H); 7.10 (s, 1H); 7.26 (s, 1H); 7.43 (d, 2H, 8 Hz); 7.48 (d, 2H, 8 Hz); 7.56 (d, 2H, 8 Hz); 7.95 (d, 2H, 8 Hz); 13.10 (s, 1H).

EXAMPLE 9

Synthesis of 4-[4-(4-bromobenzyloxy)-5,5,8,8-tet-ramethyl-5,6,7,8,-tetrahydro-2-naphthylselanylethy-nyl]benzoic acid a. Preparation of Methyl-4-[5,5,8,8-tetramethyl-4-(4-bro-mobenzyloxy)-5,6,7,8-tetrahydro-2-naphthylselanylethy-nyl]benzoate:

In a manner similar to that of Example 1f, by reacting 215 mg (0.5 mmol) of methyl 4-(4-hydroxy-5,5,8,8-tetramethyl-5,6,7,8-tetrahydro-2-naphthylselanylethynyl]benzoate with 80 mg (0.6 mmol) of potassium carbonate and 146 mg (0.6 mmol) of 4-bromobenzyl bromide. A white solid is obtained (m=320 mg; yield=100%).

b. Synthesis of 4-[5,5,8,8-tetramethyl-4-(4-bromobenzyloxy)-5,6,7,8-tetrahydro-2-naphthylselanylethynyl]benzoic acid:

In a manner similar to that of Example 1g, by reacting 320 mg (0.5 mmol) of methyl 4-[5,5,8,8-tetramethyl-4-(4-bromobenzyloxy)-5,6,7,8-tetrahydro-2-naphthylselanylethynyl]benzoate with 110 mg of sodium hydroxide. A white crystallized solid is obtained (m=240 mg; yield=66%; m.p.=265° C.).

$^1$H NMR (DMSO) 1.24 (s, 6H); 1.32 (s, 6H); 1.59 (m, 4H); 5.13 (s, 2H); 7.09 (d, 1H, 1.2 Hz); 7.25 (d, 1H, 1.2 Hz); 7.41 (d, 2H, 8.4 Hz); 7.56 (d, 4H, 7.2 Hz); 7.95 (d, 2H, 8 Hz); 13.10 (s, 1H).

EXAMPLE 10

Synthesis of 4-[5,5,8,8-tetramethyl-4-(3-methylbenzyloxy)-5,6,7,8-tetrahydro-2-naphthylselanylethynyl]benzoic acid a. Preparation of Methyl 4-[5,5,8,8-tetramethyl-4-(3-methylbenzyloxy)-5,6,7,8-tetrahydro-2-naphthylselanylethynyl]benzoate:

In a manner similar to that of Example 1f, by reacting 600 mg (1.35 mmol) of methyl 4-(4-hydroxy-5,5,8,8-tetramethyl-5,6,7,8-tetrahydro-2-naphthylselanylethynyl]benzoate with 250 mg (1.8 mmol) of potassium carbonate and 274 μL (1.5 mmol) of 3-methylbenzyl bromide. A white solid is obtained (m=708 mg; yield 96%; m.p.=102° C.).

b. Synthesis of 4-[5,5,8,8-tetramethyl-4-(3-methylbenzyloxy)-5,6,7,8-tetrahydro-2-naphthylselanylethynyl]benzoic acid:

In a similar manner to that of Example 1g, by reacting 650 mg (1.2 mmol) of methyl 4-[5,5,8,8-tetramethyl-4-(3-methylbenzyloxy)-5,6,7,8-tetrahydro-2-naphthylselanylethynyl]benzoate with 240 mg of sodium hydroxide. A yellow crystallized solid is obtained (m=600 mg; yield=94%; m.p. 225° C.).

$^1$H NMR (DMSO): 1.29 (s, 6H); 1.38 (s, 6H): 1.62-1.65 (m, 4H); 2.34 (s, 3H); 5.15 (s, 2H); 7.16-7.19 (m, 2H); 7.29-7.31 (m, 4H); 7.63 (d, J=8.2 Hz, 2H); 8.00 (d, J=8.2 Hz, 2H); 13.3 (bs, 1H).

EXAMPLE 11

Synthesis of 4-[5,5,8,8-tetramethyl-4-(4-methylbenzyloxy)-5,6,7,8-tetrahydro-2-naphthylselanylethynyl]benzoic acid a. Preparation of Methyl 4[5,5,8,8-tetramethyl-4-(4-fluorobenzyloxy)-5,6,7,8-tetrahydro-2-naphthylselanylethynyl]benzoate:

In a manner similar to that of Example 1f, by reacting 600 mg (1.35 mmol) of methyl 4-(4-hydroxy-5,5,8,8-tetramethyl-5,6,7,8-tetrahydro-2-naphthylselanylethynyl]benzoate with 250 mg (1.8 mmol) of potassium carbonate and 185 μL (1.5 mmol) of 4-fluorobenzyl bromide. A white solid is obtained (m=690 mg; yield=93%; m.p.=121° C.).

b. Synthesis of 4-[5,5,8,8-tetramethyl-4-(4-fluorobenzyloxy)-5,6,7,8-tetrahydro-2-naphthylselanylethynyl]benzoic acid:

In a manner similar to that of Example 1g, by reacting 650 mg (1.2 mmol) of methyl 4-[5,5,8,8-tetramethyl-4-(4-fluorobenzyloxy)-5,6,7,8-tetrahydro-2-naphthylselanylethynyl]benzoate with 240 mg of sodium hydroxide. A yellow crystallized solid is obtained (m=619 mg; yield=98%; m.p.=228° C.).

$^1$H NMR (DMSO): 1.14 (s, 6H); 1.21 (s, 6H); 1.45-1.49 (m, 4H); 5.02 (s, 2H); 7.02 (s, 1H); 7.08-7.15 (m, 3H); 7.39-7.42 (m, 2H); 7.47 (d, J=8.1 Hz, 2H); 7.85 (d, J=8.1 Hz, 2H); 12.9 (bs, 1H).

EXAMPLE 12

Synthesis of 4-{4-hydroxy-3-[5,5,8,8-tetramethyl-4-(4-trifluoromethylbenzyloxy)-5,6,7,8-tetrahydro-2-naphthyl]prop-1-ynyl}benzoic acid a. Preparation of 4-hydroxy-5,5,8,8-tetramethyl-5,6,7,8-tetrahydro-2-naphthalenecarbaldehyde:

30 g (106 mmol) of 3-bromo-5,5,8,8-tetramethyl-5,6,7,8-tetrahydro-1-naphthyl (Example 5a) are dissolved in 500 mL of anhydrous THF. The medium is cooled to −78° C., and 156 mL (265 mmol) of tert-butyllithium are then added dropwise. After 45 minutes at this temperature, 12.3 mL (159 mmol) of dimethylformamide are added. The mixture is warmed to room temperature and then treated with 1 N hydrochloric acid solution and extracted with ethyl acetate. The residue obtained is then purified by chromatography (eluent: 9/1 heptane/ethyl acetate). A white solid is obtained (m=16.5 g; yield=67%; m.p.=144° C.).

b. Preparation of 5,5,8,8-tetramethyl-4-(4-trifluoromethylbenzyloxy)-5,6,7,8-tetrahydro-2-naphthalenecarbaldehyde:

In a manner similar to that of Example 1c, by reacting 700 mg (3 mmol) of 4-hydroxy-5,5,8,8-tetramethyl-5,6,7,8-tetrahydro-2-naphthalenecarbaldehyde with 160 mg of sodium hydride and 789 mg (3.3 mmol) of 4-trifluoromethylbenzyl bromide. A yellow oil is obtained (m=1.15 g; yield=100%).

c. Preparation of 1-[5,5,8,8-tetramethyl-4-(4-trifluoromethylbenzyloxy)-5,6,7,8-tetrahydro-2-naphthyl]prop-2-yn-1-ol:

In a manner similar to that of Example 1f, by reacting 1.15 g (3 mmol) of 5,5,8,8-tetramethyl-4-(4-trifluoromethylbenzyloxy)-5,6,7,8-tetrahydro-2-naphthalenecarbaldehyde with 7.7 mL (7.7 mmol) of 1 N ethynylmagnesium bromide solution. A colorless oil is obtained (m=1.2 g; yield=100%).

d. Synthesis of 4-(3-hydroxy-3-[5,5,8,8-tetramethyl-4-(4-trifluoromethylbenzyloxy)-5,6,7,8-tetrahydro-2-naphthyl]prop-1-ynyl)benzoic acid:

In a manner similar to that of Example 1g, by reacting 1.2 g (2.8 mmol) of 1-[5,5,8,8-tetramethyl-4-(4-trifluoromethylbenzyloxy)-5,6,7,8-tetrahydro-2-naphthyl]prop-2-yn-1-ol with 600 mg (2.4 mmol) of 4-iodobenzoic acid in the presence of 23 mg of copper iodide and 42 mg of bis (triphenylphosphine)dichloropalladium. The desired product is obtained in the form of orange-colored crystals (m=930 mg; yield=72%, m.p. 222° C.).

$^1$H NMR (DMSO) 1.25 (s, 6H); 1.37 (s, 6H); 1.60 (m, 4H); 5.25 (s, 2H); 5.52 (s, 2H); 6.10 (d, 1H); 6.99 (s, 1H); 7.15 (s, 1H); 7.49 (d, 2H, 8 Hz); 7.73 (dd, 4H, 8 Hz, 12 Hz); 7.92 (d, 2H, 8 Hz); 13.1 (s, 1H).

EXAMPLE 13

Synthesis of 4-{3-hydroxy-3-[5,5,8,8-tetramethyl-4-(4-methylbenzyloxy)-5,6,7,8-tetrahydro-2-naphthyl]prop-1-ynyl)benzoic acid a. Preparation of 5,5,8,8-tetramethyl-4-(4-methylbenzyloxy)-5,6,7,8-tetrahydro-2-naphthalenecarbaldehyde:

In a manner similar to that of Example 1c, by reacting 700 mg (3 mmol) of 4-hydroxy-5,5,8,8-tetramethyl-5,6,7,8-tetrahydro-2-naphthalenecarbaldehyde with 160 mg of sodium hydride and 611 mg (3.3 mmol) of 4-methylbenzyl bromide. A colorless oil is obtained (m=1.12 g; yield=100%).

b. Preparation of 1-[5,5,8,8-tetramethyl-4-(4-methylbenzyloxy)-5,6,7,8-tetrahydro-2-naphthyl]prop-2-yn-1-ol:

In a manner similar to that of Example 1f, by reacting 1.12 g (3.3 mmol) of 5,5,8,8-tetramethyl-4-(4-methylbenzyloxy)-5,6,7,8-tetrahydro-2-naphthalenecarbaldehyde with 8.7 mL (8.7 mmol) of 1 N ethynylmagnesium bromide solution. A colorless oil is obtained (m=1.22 g; yield=100%).

c. Synthesis of 4-{3-hydroxy-3-[5,5,8,8-tetramethyl-4-(4-methylbenzyloxy)-5,6,7,8-tetrahydro-2-naphthyl]prop-1-ynyl}benzoic acid:

In a manner similar to that of Example 1g, by reacting 1.22 g (3.3 mmol) of 1-[5,5,8,8-tetramethyl-4-(4-methylbenzyloxy)-5,6,7,8-tetrahydro-2-naphthyl]prop-2-yn-1-ol with 680 mg (2.8 mmol) of 4-iodobenzoic acid in the presence of 27 mg of copper iodide and 49 mg of bis(triphenylphosphine)dichloropalladium. The desired product is obtained in the form of beige-colored crystals (m=900 mg; yield=67%; m.p.=219° C.).

$^1$H NMR (DMSO) 1.24 (s, 6H); 1.33 (s, 6H); 1.59 (m, 4H); 2.29 (s, 3H); 5.06 (s, 2H); 5.52 (d, 1H, 4.8 Hz); 6.10 (d, 1H, 5.6 Hz); 7.01 (d, 1H, 1.2 Hz); 7.12 (d, 1H, 0.8 Hz); 7.18 (d, 2H, 7.6 Hz); 7.37 (d, 2H, 8 Hz); 7.51 (d, 2H, 8 Hz); 7.93 (d, 2H, 8 Hz); 13.1 (s, 1H).

EXAMPLE 14

Synthesis of 4-{3-[4-(4-tert-butylbenzyloxy)-5,5,8,8-tetramethyl-5,6,7,8-tetrahydro-2-naphthyl]-3-hydroxy-prop-1-ynyl}benzoic acid a. Preparation of 4-(4-tert-butylbenzyloxy)-5,5,8,8-tetramethyl-5,6,7,8-tetrahydro-2-naphthalenecarbaldehyde:

In a manner similar to that of Example 1c, by reacting 700 mg (3 mmol) of 4-hydroxy-5,5,8,8-tetramethyl-5,6,7,8-tetrahydro-2-naphthalenecarbaldehyde with 160 mg of sodium hydride and 600 µL (3.3 mmol) of 4-tert-butylbenzyl bromide. A colorless oil is obtained (m=1.2 g; yield=100%).

b. Preparation of 1-[4-(4-tert-butylbenzyloxy)-5,5,8,8-tetramethyl-5,6,7,8-tetrahydro-2-naphthyl]-prop-2-yn-1-ol:

In a similar manner to that of Example 1f, by reacting 1.2 g (3 mmol) of 4-(4-tert-butylbenzyloxy)-5,5,8,8-tetramethyl-5,6,7,8-tetrahydro-2-naphthalenecarbaldehyde with 7.8 mL (7.8 mmol) of 1 N ethynylmagnesium bromide solution. A colorless oil is obtained (m=760 mg; yield=63%).

c. Synthesis of 4-{3-[4-(4-tert-butylbenzyloxy)-5,5,8,8-tetramethyl-5,6,7,8-tetrahydro-2-naphthyl]-3-hydroxy-prop-1-ynyl}benzoic acid:

In a manner similar to that of Example 1g, by reacting 760 mg (1.9 mmol) of 1-[4-(4-tert-butylbenzyloxy)-5,5,8,8-tetramethyl-5,6,7,8-tetrahydro-2-naphthyl]prop-2-yn-1-ol with 390 mg (1.6 mmol) of 4-iodobenzoic acid in the presence of 15 mg of copper iodide and 28 mg of bis(triphenylphosphine)dichloropalladium. The desired product is obtained in the form of white crystals (m=600 mg; yield=71%; m.p.=254° C.).

$^1$H NMR (DMSO) 1.25 (s, 6H); 1.26 (s, 9H): 1.36 (s, 6H): 1.59 (m, 4H): 5.09 (s, 2H); 5.53 (d, 1H, 5.6 Hz); 6.10 (d, 1H, 6.4 Hz); 7.05 (s, 1H): 7.13 (s, 1H); 7.39 (dd, 4H, 8 Hz, 16 Hz); 7.53 (d, 2H, 8.4 Hz); 7.93 (d, 2H, 8.4 Hz); 13.10 (s, 1H).

EXAMPLE 15

Synthesis of 4-{3-[4-(4-fluorobenzyloxy)-5,5,8,8-tetramethyl-5,6,7,8-tetrahydro-2-naphthyl]-3-hydroxy-prop-1-ynyl}benzoic acid a. Preparation of 4-(4-fluorobenzyloxy)-5,5,8,8-tetramethyl-5,6,7,8-tetrahydro-2-naphthalenecarbaldehyde:

In a manner similar to that of Example 1c, by reacting 700 mg (3 mmol) of 4-hydroxy-5,5,8,8-tetramethyl-5,6,7,8-tetrahydro-2-naphthalenecarbaldehyde with 160 mg of sodium hydride and 410 µL (3.3 mmol) of 4-fluorobenzyl bromide. A colorless oil is obtained (m=1.2 g; yield=100%).

b. Preparation of 1-[4-(4-fluorobenzyloxy)-5,5,8,8-tetramethyl-5,6,7,8-tetrahydro-2-naphthyl]prop-2-yn-1-ol:

In a manner similar to that of Example 1f, by reacting 1.0 g (2.9 mmol) of 4-(4-fluorobenzyloxy-5,5,8,8-tetramethyl-5,6,7,8-tetrahydro-2-naphthalenecarbaldehyde with 4.5 mL (4.5 mmol) of 1 N ethynylmagnesium bromide solution. A colorless oil is obtained (m=580 mg; yield=55%).

c. Synthesis of 4-(3-[4-(4-fluorobenzyloxy)-5,5,8,8-tetramethyl-5,6,7,8-tetrahydro-2-naphthyl]-3-hydroxy-prop-1-ynyl}benzoic acid:

In a manner similar to that of Example 1g, by reacting 580 mg (1.6 mmol) of 1-[4-(4-fluorobenzyloxy)-5,5,8,8-tetramethyl-5,6,7,8-tetrahydro-2-naphthyl]prop-2-yn-1-ol with 330 mg (1.3 mmol) of 4-iodobenzoic acid in the presence of 12 mg of copper iodide and 23 mg of bis(triphenylphosphine)dichloropalladium. The desired product is obtained in the form of beige-colored crystals (m=420 mg; yield=67%; m.p. 188° C.).

$^1$H NMR (DMSO) 1.24 (s, 6H); 1.59 (s, 6H); 5.10 (s, 2H); 5.52 (d, 1H, 4.3 Hz); 6.10 (s, 1H); 7.00 (d, 1H, 1.2 Hz); 7.13 (d, 1H, 1.2 Hz), 7.19 (t, 2H, 8.8 Hz); 7.50 (m. 4H); 7.92 (d, 2H, 8.4 Hz).

EXAMPLE 16

Synthesis of 4-(E)-3-[4-(4-fluorobenzyloxy)-5,5,8,8-tetramethyl-5,6,7,8-tetrahydro-2-naphthyl]-3-oxopropenyl}benzoic acid a. Preparation of 1-(4-hydroxy-5,5,8,8-tetramethyl-5,6,7,8-tetrahydro-2-naphthyl)ethanone:

5 g (22 mmol) of 4-hydroxy-5,5,8,8-tetramethyl-5,6,7,8-tetrahydro-2-naphthalenecarbaldehyde (Example 16a) are dissolved in 150 mL of THF. The medium is cooled to 0° C. and 15 mL (45 mmol) of 3M methylmagnesium bromide solution are then added. After 30 minutes, the medium is treated with saturated ammonium chloride solution and then extracted with ethyl acetate. The residue obtained is dissolved in 40 mL of dichloromethane. A solution of 6.5 mL of DMSO (84 mmol) in 50 mL of dichloromethane is then added slowly to a solution, prepared beforehand, of 3.75 mL (43 mmol) of oxalyl chloride in 100 mL of dichloromethane at −78° C. The solution containing the product obtained previously is then added to this reaction medium very slowly, followed by addition of 23 mL (165 mmol) of triethylamine. The reaction medium is warmed slowly to room temperature and is then treated with saturated ammonium chloride solution and extracted with dichloromethane. The residue is purified by chromatography (eluent: 9/1 heptane/ethyl acetate). A thick yellow oil is obtained (m=2.6 g; yield 51%).

b. Preparation of Methyl 4-[(E)-3-(4-hydroxy-5,5,8,8-tetramethyl-5,6,7,8-tetrahydro-2-naphthyl)-3-oxopropenyl]benzoate:

1.4 g (4.9 mmol) of 1-(4-hydroxy-5,5,8,8-tetramethyl-5,6,7,8-tetrahydro-2-naphthyl)ethanone are dissolved in 50 mL of methanol. 660 mg (4.4 mmol) of 4-carboxybenzaldehyde and 2.3 mL (20 mmol) of 47% KOH solution are then added. The reaction medium is stirred at 65° C. for 48 hours, and then cooled and acidified, and finally extracted with ethyl acetate. The residue obtained is then dissolved in 50 mL of methanol and 1 mL of concentrated sulfuric acid. The reaction medium is stirred at reflux for 12 hours and then cooled, hydrolyzed, and extracted with dichloromethane. The residue obtained is purified by chromatography (eluent: 85/15 heptane/ethyl acetate). A yellow crystallized solid is obtained (m=390 mg; yield=20%).

c. Preparation of Methyl 4-[{(E)-3-[4-(4-fluorobenzyloxy-5,5,8,8-tetramethyl-5,6,7,8-tetrahydro-2-naphthyl]-3-oxopropenyl}benzoate:

In a manner similar to Example 1f, by reacting 340 mg (0.85 mmol) of methyl 4-[(E)-3-(4-hydroxy-5,5,8,8-tetramethyl-5,6,7,8-tetrahydro-2-naphthyl)-3-oxopropenyl]benzoate with 140 mg (1 mmol) of potassium carbonate and 120 μL (1 mmol) of 4-fluorobenzyl bromide. The product is obtained in the form of yellow crystals (m=320 mg; yield=75%; m.p.=142° C.).

d. Synthesis of 4-{(E)-3-[4-(4-fluorobenzyloxy)-5,5,8,8-tetramethyl-5,6,7,8-tetrahydro-2-naphthyl]-3-oxopropenyl}benzoic acid:

In a manner similar to that of Example 1g, by reacting 320 mg (0.6 mmol) of methyl 4-{(E)-3-[4-(4-fluorobenzyloxy)-5,5,8,8-tetramethyl-5,6,7,8-tetrahydro-2-naphthyl]-3-oxopropenyl}benzoate with 128 mg (3 mmol) of sodium hydroxide. The desired product is obtained in the form of a white crystallized solid (m=170 mg; yield=55%; m.p.=241° C.).

$^1$H NMR (DMSO) 1.33 (S, 6H); 1.35 (s, 6H); 1.63 (m, 4H); 5.22 (s, 2H); 7.27 (t, 2H, 8 Hz); 7.52 (s, 1H); 7.58 (dd, 2H, 8 Hz, 2.4 Hz); 7.78 (s, 2H); 8.01 (s, 4H).

EXAMPLE 17

Synthesis of 6-{1-[4-(4-fluorobenzyloxy)-5,5,8,8-tetramethyl-5,6,7,8-tetrahydro-2-naphthyl]methanoyl}naphthalene-2-carboxylic acid a. Preparation of 4-ethoxymethoxy-5,5,8,8-tetramethyl-5,6,7,8-tetrahydro-2-naphthalene boronic acid:

8.9 g (26 mmol) of 7-bromo-5-ethoxymethoxy-1,1,4,4-tetramethyl-1,2,3,4-tetrahydronaphthalene (Example 5b) are dissolved in 200 mL of anhydrous THF and the mixture is cooled to −78° C. 12.5 mL (31 mmol) of 2.5M butyllithium solution are added and the mixture is stirred for 1 hour. 7.2 mL (31 mmol) of triisopropyl borate are then added and the reaction medium is stirred at this temperature for 1 hour, then warmed to room temperature and treated with saturated ammonium chloride solution. The residue obtained after extraction is washed with heptane. A white powder is obtained (m=6.8 g; yield=85%).

b. Preparation of Methyl 6-[1-(4-ethoxymethoxy-5,5,8,8-tetramethyl-5,6,7,8-tetrahydro-2-naphthyl)methanoyl]-2-naphthalenecarboxylate:

5 g (16 mmol) of 4-ethoxymethoxy-5,5,8,8-tetramethyl-5,6,7,8-tetrahydro-2-naphthalene boronic acid are dissolved in 100 mL of toluene. 26 g (80 mmol) of caesium carbonate are added and the medium is degassed for 15 minutes with a flow of nitrogen. 14 mg (0.8 mmol) of palladium chloride are added, followed by 5.47 g (22 mmol) of methyl 6-chlorocarbonyl-2-naphthalenecarboxylate in 1 g portions. The reaction medium is refluxed for 15 hours and then hydrolysed and extracted with ethyl acetate. The residue obtained is purified by chromatography (eluent: 9/1 heptane/ethyl acetate). The product is then recrystallized from an ethyl acetate/heptane mixture (m=4.3 g; yield=59%; m.p.=96° C.).

c. Preparation of Methyl 6-[1-(4-hydroxy-5,5,8,8-tetramethyl-5,6,7,8-tetrahydro-2-naphthyl)methanoyl]-2-naphthalenecarboxylate:

3.5 g (7.6 mmol) of methyl 6-[1-(4-ethoxymethoxy-5,5,8,8-tetramethyl-5,6,7,8-tetrahydro-2-naphthyl)methanoyl]-2-naphthalenecarboxylate are dissolved in 50 mL of THF and 100 mL of methanol. 1 mL of concentrated sulfuric acid is added and the reaction medium is heated at 80° C. for 2 hours and then cooled and hydrolyzed. A white solid is obtained (m=2.6 g; yield=84%; m.p.=222° C.).

d. Preparation of Methyl 6-(1-[4-(4-fluorobenzyloxy)-5,5,8,8-tetramethyl-5,6,7,8-tetrahydro-2-naphthyl]methanoyl}-2-naphthalenecarboxylate:

In a manner similar to that of Example 1f, by reacting 1.5 g (3.6 mmol) of methyl 6-[1-(4-hydroxy-5,5,8,8-tetramethyl-5,6,7,8-tetrahydro-2-naphthyl)methanoyl]-2-naphthalenecarboxylate with 600 mg (4.5 mmol) of potassium carbonate and 540 μL (4.3 mmol) of 4-fluorobenzyl bromide. The product is obtained in the form of white crystals (m=320 mg; yield 98%; mp.=179° C.).

e. Synthesis of 6-(1-[4-(4-fluorobenzyloxy)-5,5,8,8-tetramethyl-5,6,7,8-tetrahydro-2-naphthyl]methanoyl)-2-naphthalenecarboxylic acid:

In a manner similar to that of Example 1g, by reacting 250 mg (0.5 mmol) of methyl 6-{1-[4-(4-fluorobenzyloxy)-5,5,8,8-tetramethyl-5,6,7,8-tetrahydro-2-naphthyl]methanoyl}-2-naphthalenecarboxylate with 40 mg of sodium hydroxide. A white crystallized solid is obtained (m=235 mg; yield=66%; m.p.=277° C.).

$^1$H NMR (DMSO) 1.24 (s, 6H); 1.39 (s, 6H); 1.63-1.66 (m, 4H); 5.15 (s, 2H); 7.20-7.27 (m, 3H); 7.41 (s, 1H): 7.49-7.52 (m, 2H), 7.89 (d, J=8.5 Hz, 1H); 8.06 (d, J=8.5 Hz, 1H); 8.19 (d, J=8.7 Hz, 1H); 8.26 (d, J=8.6 Hz, 1H); 8.37 (s, 1H); 8.70 (s, 1H).

EXAMPLE 18

Synthesis of 6-{1-[4-(4-fluorobenzyloxy)-5,5,8,8-tetramethyl-5,6,7,8-tetrahydro-2-naphthyl]-1-hydroxymethyl}-2-naphthalenecarboxylic acid 245 mg (0.5 mmol) of 6-{1-[4-(4-fluorobenzyloxy)-5,5,8,8-tetramethyl-5,6,7,8-tetrahydro-2-naphthyl]methanoyl}-2-naphthalenecarboxylate are dissolved in 5 mL of THF and 5 mL of methanol, and 28 mg (0.7 mmol) of sodium borohydride are added. The medium is stirred for 1 hour, and then treated with saturated ammonium chloride solution. The residue obtained after extraction is purified by chromatography: a white solid is obtained (m=220 mg; yield=89%; m.p.=212° C.).

¹H NMR (DMSO): 1.20 (s, 6H); 1.27 (s, 6H); 1.53-1.55 (m, 4H); 5.01 (s, 2H); 5.79 (s, 1H); 5.98 (bs, 1H); 6.89 (s, 1H); 7.09-7.17 (m, 3H); 7.44-7.48 (m, 2H); 7.56 (d, J=8.6 Hz, 1H); 7.94-8.02 (m, 4H); 8.53 (s, 1H).

EXAMPLE 19

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference agonist. The inhibitory products displace the agonist from its site, thus preventing activation of the receptor. The activity is measured by quantifying the reduction in light produced. This measurement makes it possible to determine the inhibitory activity of the compounds according to the invention.

Determination of the Kdapp:

In this study, a constant is determined which represents the affinity of the molecule for the receptor. Since this value can fluctuate depending on the basal activity and the expression of the receptor, it is referred to as the Kdapparent (KdApp).

To determine this constant, "crossed curves" of the test product against a reference agonist, 4-[2-(5,5,8,8-tetramethyl-5,6,7,8-tetrahydro-2-naphthyl)propenyl]benzoic acid, are performed in 96-well plates. The test product is used at 10 concentrations and the reference agonist at 7 concentrations. In each well, the cells are in contact with a concentration of the test product and a concentration of the reference agonist, 4-[2-(5,5,8,8-tetramethyl-5,6,7,8-tetrahydro-2-naphthyl)propenyl]benzoic acid. Measurements are also taken for the total agonist (4-[2-(5,5,8,8-tetramethyl-5,6,7,8-tetrahydro-2-naphthyl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("*quantitation in receptor pharmacology*" Terry P. Kenakin, *Receptors and Channels*, 2001, 7, 371-385).

In the case of an antagonist, an $IC_{50}$ value (concentration that inhibits 50% of the activity) is calculated by plotting the curve of the product at the concentration of the reference ligand that gives 80% activation.

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10 000 cells per well in 100 μl of DMEM medium without phenol red, and supplemented with 10% defatted calf serum. The plates are then incubated at 37° C. and 7% $CO_2$ for 4 hours.

The various dilutions of the test products, of the reference ligand (4-[2-(5,5,8,8-tetramethyl-5,6,7,8-tetrahydro-2-naphthyl)propenyl]benzoic acid), of the 100% control (100 nM 4-[2-(5,5,8,8-tetramethyl-5,6,7,8-tetrahydro-2-naphthyl) propenyl]benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 μl per well. The plates are then incubated for 18 hours at 37° C. and 7% $CO_2$.

The culture medium is removed by turning over and 100 μl of a 1:1 PBS/luciferine mixture is added to each well. After 5 minutes, the plates are read using the luminescence detector.

|  | RAR alpha | | RAR beta | | RAR gamma | |
| --- | --- | --- | --- | --- | --- | --- |
|  | Kdapp (nM) | $IC_{50}$ (nM) | Kdapp (nM) | $IC_{50}$ (nM) | Kdapp (nM) | $IC_{50}$ (nM) |
| Ex 1 | 8 | 14 | 4 | 6.5 | 2 | 5 |
| Ex 3 | 15 | 26.25 | 30 | 48 | 4 | 10 |
| Ex 4 | 2 | 3.5 | 4 | 6.4 | 1 | 2.5 |
| Ex 5 | 2 | 3.5 | 1 | 1.6 | 1 | 2.5 |
| Ex 10 | 30 | 52.5 | 15 | 24 | 4 | 10 |
| Ex 11 | 8 | 14 | 4 | 6.4 | 1 | 2.5 |

The results obtained with the compounds according to the invention clearly show Kdapp values ≦100 nM and an $IC_{50}$ value ≦100 nM for at least one of the receptor subtypes, this clearly demonstrating a reduction in the signal, and in the luminescence in the presence of the reference agonist. The compounds according to the invention are thus clearly inhibitors of retinoic acid receptors (RAR).

EXAMPLE 20

FORMULATION EXAMPLES

This example illustrates various specific formulations based on the compounds according to the invention.

A - ENTERAL ROUTE:

(a) 0.2 g tablet:

| | |
| --- | --- |
| Compound of Example 16 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | |
| --- | --- |
| Compound of Example 17 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
| --- | --- |
| Compound of Example 9 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules:

| | |
| --- | --- |
| Compound of Example 2 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

-continued

B - PARENTERAL ROUTE:

(a) Composition:

| Compound of Example 3 | 0.002 g |
| Ethyl oleate | qs 10 g |

(b) Composition:

| Compound of Example 1 | 0.05% |
| Polyethylene glycol | 20% |
| 0.9% NaCl solution | qs 100 |

(c) Composition:

| Compound of Example 3 | 2.5% |
| Polyethylene glycol 400 | 20% |
| 0.9% NaCl solution | qs 100 |

(d) Injectable cyclodextrin composition:

| Compound of Example 3 | 0.1 mg |
| β-Cyclodextrin | 0.10 g |
| Water for injection | qs 10.00 g |

C - TOPICAL ROUTE:

(a) Ointment:

| Compound of Example 12 | 0.020 g |
| Isopropyl myristate | 81.700 g |
| Liquid petroleum jelly fluid | 9.100 g |
| Silica ("Aerosil 200" sold by Degussa) | 9.180 g |

(b) Ointment:

| Compound of Example 15 | 0.300 g |
| White petroleum jelly codex | qs 100 g |

(c) Nonionic water-in-oil cream:

| Compound of Example 10 | 0.100 g |
| Mixture of emulsifying lanolin alcohols, waxes and oils ("Anhydrous Eucerin" sold by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| Compound of Example 9 | 0.100 g |
| Polyethylene glycol (PEG 400) | 69.900 g |
| 95% ethanol | 30.000 g |

(e) Hydrophobic ointment:

| Compound of Example 4 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300 000 cst" sold by Goldschmidt) | qs 100 g |

(f) Nonionic oil-in-water cream:

| Compound of Example 6 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A bicyclic compound having the structural formula (I):

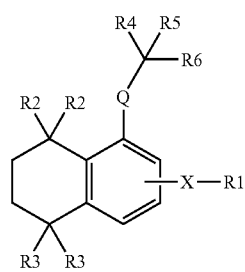

(I)

in which $R_1$ is a radical of formulae (a) to (c) below:

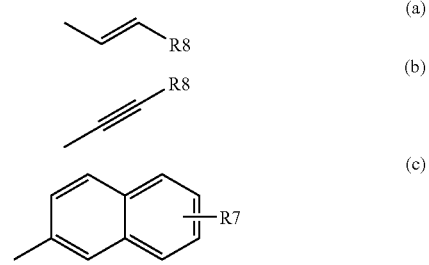

wherein $R_7$ and $R_8$ are as defined below; each of the radicals $R_2$ and $R_3$, which may be identical or different, is a hydrogen atom or an alkyl radical having from 1 to 6 carbon atoms; X is an Se atom, —CHOH, —CH$_2$ or —C═O; Q is an oxygen atom, a sulfur atom, CH$_2$, —NH or —NR$_9$—, wherein $R_9$ is as defined below; $R_4$ and $R_5$, which may be identical or different, are each a hydrogen atom, an alkyl radical having from 1 to 6 carbon atoms, or together form an oxo radical; $R_6$ is a phenyl radical or a naphthyl radical, $R_6$ being optionally substituted with one or more radicals selected from among an alkyl radical having from 1 to 6 carbon atoms, an —OR$_{10}$ radical, a halogen atom, —CF$_3$, —NH$_2$ and a nitrogen atom mono- or disubstituted with an alkyl radical having from 1 to 6 carbon atoms, wherein $R_{10}$ is as defined below; $R_7$ is a radical —COR$_{11}$, wherein $R_{11}$ is as defined below; $R_8$ is a radical:

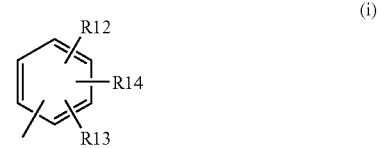

(i)

wherein $R_{12}$, $R_{13}$ and $R_{14}$ are as defined below; $R_9$ is an alkyl radical having from 1 to 6 carbon atoms; $R_{10}$ is a hydrogen atom or an alkyl radical having from 1 to 6 carbon atoms; $R_{11}$ is a radical —OR$_{15}$ or a radical —NR$_{15}$R$_{16}$, wherein $R_{15}$ and $R_{16}$ are as defined below; $R_{12}$ and $R_{13}$, which may be identical or different, are each a hydrogen atom, a halogen atom, an alkyl radical having from 1 to 6 carbon atoms or a radical —OR$_{17}$, wherein $R_{17}$ is as defined below; $R_{14}$ is a radical —COR$_{18}$, wherein $R_{18}$ is as defined below; $R_{15}$, $R_{16}$ and $R_{17}$, which may be identical or different, are each a hydrogen atom or an alkyl radical having from 1 to 6 carbon atoms; $R_{18}$ is a radical $-OR_{19}$, or a radical $-NR_{19}R_{20}$, wherein $R_{19}$ and $R_{20}$ are as defined below; $R_{19}$ is a hydrogen atom or an alkyl radical having from 1 to 6 carbon atoms; $R_{20}$ is a hydrogen atom, an alkyl radical having from 1 to 6 carbon atoms, or —OH, or a salt, isomer or mixture thereof.

2. The bicyclic compound as defined by claim 1, wherein formula (I), $R_1$ is a radical (a).

3. The bicyclic compound as defined by claim 1, wherein formula (I), $R_1$ is a radical (b).

4. The bicyclic compound as defined by claim 1, wherein formula (I), $R_1$ is a radical (c).

5. The bicyclic compound as defined by claim 1, wherein formula (I), X is Se.

6. The bicyclic compound as defined by claim 1, wherein formula (I), X is —CHOH.

7. The bicyclic compound as defined by claim 1, wherein formula (I), X is —CH$_2$.

8. The bicyclic compound as defined by claim 1, wherein formula (I), X is C=O.

9. The bicyclic compound as defined by claim 1, wherein formula (I), $R_6$ is a phenyl radical.

10. The bicyclic compound as defined by claim 1, wherein formula (I), $R_6$ is a naphthyl radical.

11. A salt of the bicyclic compound (I) as defined by claim 1.

12. An alkali or alkaline-earth metal, or zinc or organic amine salt of the bicyclic compound (I) as defined in claim 1.

13. The bicyclic compound as defined by claim 1, containing at least one alkyl radical selected from the group consisting of methyl, ethyl, propyl, isopropyl, butyl, tert-butyl, pentyl and hexyl radicals.

14. The bicyclic compound as defined by claim 1, containing at least one fluorine, chlorine and/or bromine atom.

15. The bicyclic compound as defined by claim 1, containing at least one nitrogen, oxygen, sulfur or selenium hetero atom.

16. The bicyclic compound as defined by claim 1, selected from the group consisting of:
 4-[4-(3-fluorobenzyloxy)-5,5,8,8-tetramethyl-5,6,7,8-tetrahydro-2-naphthylselanylethynyl]benzoic acid,
 4-[5,5,8,8-tetramethyl-4-(4-methylbenzyloxy)-5,6,7,8-tetrahydro-2-naphthylselanylethynyl]benzoic acid,
 4-[4-(4-tert-butylbenzyloxy)-5,5,8,8-tetramethyl-5,6,7,8-tetrahydro-2-naphthylselanylethynyl]benzoic acid,
 4-[4-(3,4-difluorobenzyloxy)-5,5,8,8-tetramethyl-5,6,7,8-tetrahydro-2-naphthylselanylethynyl]benzoic acid,
 4-[4-(2,4-difluorobenzyloxy)-5,5,8,8-tetramethyl-5,6,7,8-tetrahydro-2-naphthylselanylethynyl]benzoic acid,
 4-[5,5,8, 8-tetramethyl-4-(4-trifluoromethylbenzyloxy)-5,6,7,8-tetrahydro-2-naphthylselanylethynyl]benzoic acid,
 4-[5,5,8,8-tetramethyl-4-(2-naphthylmethoxy)-5,6,7,8-tetrahydro-2-naphthylselanylethynyl]benzoic acid,
 4-[4-(4-chlorobenzyloxy)-5,5,8,8-tetramethyl-5,6,7,8-tetrahydro-2-naphthylselanylethynyl]benzoic acid,
 4-[4-(4-bromobenzyloxy)-5,5,8,8-tetramethyl-5,6,7,8-tetrahydro-2-naphthylselanylethynyl]benzoic acid,
 4-[5,5,8,8-tetramethyl-4-(3-methylbenzyloxy)-5,6,7,8-tetrahydro-2-naphthylselanylethynyl]benzoic acid,
 4-[4-(4-fluorobenzyloxy)-5,5,8,8-tetramethyl-5,6,7,8-tetrahydro-2-naphthylselanylethynyl]benzoic acid,
 4-{3-hydroxy-3-[5,5,8,8-tetramethyl-4-(4-trifluoro methylbenzyloxy)-5,6,7,8-tetrahydro-2-naphthyl]prop-1-ynyl}benzoic acid,
 4-{3-hydroxy-3-[5,5,8,8-tetramethyl-4-(4-tert-butylbenzyloxy)-5,6,7,8-tetrahydro-2-naphthyl]prop-1-ynyl}benzoic acid,
 4-{3-hydroxy-3-[5,5,8,8-tetramethyl-4-(4-methylbenzyloxy)-5,6,7,8-tetrahydro-2- methyl[prop-1-ynyl}benzoic acid,
 4-{3-[4-(4-tert-butylbenzyloxy)-5,5,8,8-tetramethyl-5,6,7,8-tetrahydro-2-naphthyl]-3-hydroxyprop-1-ynyl}benzoic acid,
 4-{(E)-3-[4-(4-fluorobenzyloxy)-5,5,8,8-tetramethyl-5,6,7,8-tetrahydro-2-naphthyl]-3-oxopropenyl}benzoic acid,
 6-{1-[4-(4-fluorobenzyloxy)-5,5,8,8-tetramethyl-5,6,7,8-tetrahydro-2-naphthyl]methanoyl}naphthalene-2-carboxylic acid,
 6-{1-[4-(4-fluorobenzyloxy)-5,5,8,8-tetramethyl-5,6,7,8-tetrahydro-2-naphthyl]-1-hydroxymethyl}naphthalene-2-carboxylic acid,
 4-{3-[4-(4-fluorobenzylamino)-5,5,8,8-tetramethyl-5,6,7,8-tetrahydro-2-naphthyl]-3-hydroxypropenyl}benzoic acid,
 4-(3-{4-[(4-fluorobenzyl)methylamino]-5,5,8,8-tetramethyl-5,6,7,8-tetrahydro-2-naphthyl}-3-oxopropenyl) benzoic acid,
 4-{3-[4-(4-fluorobenzylamino)-5,5,8,8-tetramethyl-5,6,7,8-tetrahydro-2-naphthyl]-3-hydroxyprop-1-ynyl}benzoic acid,
 4-{3-[4-(4-fluorobenzylamino)-5,5,8,8-tetramethyl-5,6,7,8-tetrahydro-2-naphthyl]-3-oxopropenyl}benzoic acid,
 4-(3-{4-[(4-fluorobenzyl)methylamino]-5,5,8,8-tetramethyl-5,6,7,8-tetrahydro-2-naphthyl}-3-hydroxypropenyl)benzoic acid,
 4-(3-{4-[(4-fluorobenzyl)methylamino]-5,5,8,8-tetramethyl-5,6,7,8-tetrahydro-2-naphthyl}-3-hydroxyprop-1-ynyl)benzoic acid,
 4-{3-[4-(4-fluorobenzylsulfanyl)-5,5,8,8-tetramethyl-5,6,7,8-tetrahydro-2-naphthyl]-3-hydroxypropenyl}benzoic acid,
 4-{3-[4-(4-fluorobenzylsulfanyl)-5,5,8,8-tetramethyl-5,6,7,8-tetrahydro-2-naphthyl]-3-oxopropenyl}benzoic acid,
 4-{3-[4-(4-fluorobenzylsulfanyl)-5,5,8,8-tetramethyl-5,6,7,8-tetrahydro-2-naphthyl]-3-hydroxyprop-1-ynyl}benzoic acid,
 4-{3-[4-(4-fluorobenzylamino)-5,5,8,8-tetramethyl-5,6,7,8-tetrahydro-2-naphthyl]-3-hydroxypropenyl}-2-hydroxybenzoic acid,
 4-(3-{4-[(4-fluorobenzyl)methylamino]tetramethyl-5,6,7,8-tetrahydro-2-naphthyl}oxopropenyl)-2-hydroxybenzoic acid,
 4-{3-[4-(4-fluorobenzylamino)-5,5,8,8-tetramethyl-5,6,7,8-tetrahydro-2-naphthyl]-3-hydroxyprop-1-ynyl}-2-hydroxybenzoic acid,
 4-{3-[4-(4-fluorobenzylamino)-5,5,8,8-tetramethyl-5,6,7,8-tetrahydro-2-naphthyl]-3-oxopropenyl}-2-hydroxybenzoic acid,
 4-(3-{4-[(4-fluorobenzyl)methylamino]-5,5,8,8-tetramethyl-5,6,7,8-tetrahydro-2-naphthyl}-3-hydroxypropenyl)-2-hydroxybenzoic acid,
 4-(3-{4-[(4-fluorobenzyl)methylamino]-5,5,8,8-tetramethyl-5,6,7,8-tetrahydro-2-naphthyl}-3-hydroxyprop-1-ynyl)-2-hydroxybenzoic acid,
 4-{3-[4-(4-fluorobenzylsulfanyl)-5,5,8,8-tetramethyl-5,6,7,8-tetrahydro-2-naphthyl]-3-hydroxypropenyl}-2-hydroxybenzoic acid, 4-{3-[4-(4-fluorobenzylsulfanyl)-5,5,8,8-tetramethyl-5,6,7,8-tetrahydro-2-naphthyl]-3-oxopropenyl}-2-hydroxybenzoic acid, 4-{3-[4-(4-fluorobenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-fluorobenzyloxy)-5,5,8,8-tetramethyl-5,6,7,8-tetrahydro-2-naphthyl]-3-hydroxypropenyl}-2-hydroxybenzoic acid, 4-{3-[4-(4-fluorobenzyloxy)-5,5,8,8-tetramethyl-5,6,7,8-tetrahydro-2-naphthyl]-3-oxopropenyl}-2-hydroxybenzoic acid, 4-{3-[4-(4-fluorobenzyloxy)-5,5,8,8-tetramethyl-5,6,7,8-tetrahydro-2-naphthyl]-3-hydroxyprop-1-ynyl}-2-hydroxybenzoic acid, 4-{3-[4-(4-fluorobenzoylamido)-5,5,8,8-tetramethyl-5,6,7,8-tetrahydro-2-naphthyl]-3-hydroxypropenyl}benzoic acid, 4-(3-{4-[(4-fluoro)methylbenzoylamido]-5,5,8,8-tetramethyl-5,6,7,8-tetrahydro-2-naphthyl}-3-oxopropenyl)benzoic acid, 4-{3-[4-(4-fluorobenzoylamido)-5,5,8,8-tetramethyl-5,6,7,8-tetrahydro-2-naphthyl]-3-hydroxyprop-1-ynyl}benzoic acid, -(3-{4-[(4-fluoro)methylbenzoylamido]-5,5,8,8-tetramethyl-5,6,7,8-tetrahydro-2-naphthyl]-3-hydroxypropenyl)benzoic acid, 4-{3-[4-(4-fluorobenzoylamido)-5,5,8,8-tetramethyl-5,6,7,8-tetrahydro-2-naphthyl]-3-oxopropenyl}benzoic acid, 4-(3-{4-[(4-fluoro)methylbenzoylamido]-5,5,8,8-tetramethyl-5,6,7,8-tetrahydro-2-naphthyl}hydroxyprop-1-ynyl)benzoic acid, 4-(3-{4-[1-(4-fluorophenyl)-1-methylethoxy]-5,5,8,8-tetramethyl-5,6,7,8-tetrahydro-2-naphthyl}-3-hydroxypropenyl)benzoic acid, 4-(3-{4-[1-(4-fluorophenyl)-1-methylethoxy]-5,5,8,8-tetramethyl-5,6,7,8-tetrahydro-2-naphthyl}-3-oxopropenyl)benzoic acid, 4-(3-{4-[1-(4-fluorophenyl)-1-methylethoxy]-5,5,8,8-tetramethyl-5,6,7,8-tetrahydro-2-naphthyl}-3-hydroxyprop-1-ynyl)benzoic acid, 4-{3-[4-(4-methylbenzylamino)-5,5,8,8-tetramethyl-5,6,7,8-tetrahydro-2-naphthyl]-3-hydroxypropenyl}benzoic acid, 4-(3-{4-[(4-methylbenzyl)methylamino]-5,5,8,8-tetramethyl-5,6,7,8-tetrahydro-2-naphthyl}-3-oxopropenyl)benzoic acid, 4-{3-[4-(4-methylbenzylamino)-5,5,8,8-tetramethyl-5,6,7,8-tetrahydro-2-naphthyl]-3-hydroxyprop-1-ynyl}benzoic acid, 4-{3-[4-(4-methylbenzylamino)-5,5,8,8-tetramethyl-5,6,7,8-tetrahydro-2-naphthyl]-3-oxopropenyl}benzoic acid, 4-(3-{4-[(4-methylbenzyl)methylamino]-5,5,8,8-tetramethyl-5,6,7,8-tetrahydro-2-naphthyl}-3-hydroxypropenyl)benzoic acid, 4-(3-{4-[(4-methylbenzyl)methylamino]-5,5,8,8-tetramethyl-5,6,7,8-tetrahydro-2-naphthyl}-3-hydroxyprop-1-ynyl)benzoic acid, 4-{3-[4-(4-methylbenzylsulfanyl)-5,5,8,8-tetramethyl-5,6,7,8-tetrahydro-2-naphthyl]-3-hydroxypropenyl}benzoic acid, 4-{3-[4-(4-methylbenzylsulfanyl)-5,5,8,8-tetramethyl-5,6,7,8-tetrahydro-2-naphthyl]-3-oxopropenyl}benzoic acid, 4-{3-[4-(4-methylbenzylsulfanyl)-5,5,8,8-tetramethyl-5,6,7,8-tetrahydro-2-naphthyl]-3-hydroxyprop-1-ynyl}benzoic acid, 4-{3-[4-(4-methylbenzylamino)-5,5,8,8-tetramethyl-5,6,7,8-tetrahydro-2-naphthyl]-3-hydroxypropenyl}-2-hydroxybenzoic acid, 4-(3-{4-[(4-methylbenzyl)methylamino]-5,5,8,8-tetramethyl-5,6,7,8-tetrahydro-2-naphthyl}-3-oxopropenyl)-2-hydroxybenzoic acid, 4-{3-[4-(4-methylbenzylamino)-5,5,8,8-tetramethyl-5,6,7,8-tetrahydro-2-naphthyl]-3-hydroxyprop-1-ynyl}-2-hydroxybenzoic acid, 4-{3-[4-(4-methylbenzylamino)-5,5,8,8-tetramethyl-5,6,7,8-tetrahydro-2-naphthyl]-3-oxopropenyl}-2-hydroxybenzoic acid, 4-(3-{4-[(4-methylbenzyl)methylamino]-5,5,8,8-tetramethyl-5,6,7,8-tetrahydro-2-naphthyl}-3-hydroxypropenyl)-2-hydroxybenzoic acid, 4-(3-{4-[(4-methylbenzyl)methylamino]-5,5,8,8-tetramethyl-5,6,7,8-tetrahydro-2-naphthyl}-3-hydroxyprop-1-ynyl)-2-hydroxybenzoic acid, 4-{3-[4-(4-methylbenzylsulfanyl)-5,5,8,8-tetramethyl-5,6,7,8-tetrahydro-2-naphthyl]-3-hydroxypropenyl}-2-hydroxybenzoic acid, 4-{3-[4-(4-methylbenzylsulfanyl)-5,5,8,8-tetramethyl-5,6,7,8-tetrahydro-2-naphthyl]-3-oxopropenyl}-2-hydroxybenzoic acid, 4-{3-[4-(4-methylbenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-methylbenzyloxy)-5,5,8,8-tetramethyl-5,6,7,8-tetrahydro-2-naphthyl]-3-hydroxypropenyl}-2-hydroxybenzoic acid, 4-{3-[4-(4-methylbenzyloxy)-5,5,8,8-tetramethyl-5,6,7,8-tetrahydro-2-naphthyl]-3-oxopropenyl}-2-hydroxybenzoic acid, 4-{3-[4-(4-methylbenzyloxy)-5,5,8,8-tetramethyl-5,6,7,8-tetrahydro-2-naphthyl]-3-hydroxyprop-1-ynyl}-2-hydroxybenzoic acid, 4-[3-(4-{[1-(4-methylphenyl)methanoyl]amino}-5,5,8,8-tetramethyl-5,6,7,8-tetrahydro-2-naphthyl)-3-hydroxypropenyl]benzoic acid, 4-[3-(4-{[1-(4-methylphenyl)methanoyl]methylamino}-5,5,8,8-tetramethyl-5,6,7,8-tetrahydro-2-naphthyl)-3-oxopropenyl]benzoic acid, 4-[3-(4-{[1-(4-methylphenyl)methanoyl]amino}-5,5,8,8-tetramethyl-5,6,7,8-tetrahydro-2-naphthyl)-3-hydroxyprop-1-ynyl]benzoic acid, 4-[3-(4-{[1-(4-methylphenyl)methanoyl]methylamino}-5,5,8,8-tetramethyl-5,6,7,8-tetrahydro-2-naphthyl)-3-hydroxypropenyl]benzoic acid, 4-[3-(4-{[1-(4-methylphenyl)methanoyl]amino}-5,5,8,8-tetramethyl-5,6,7,8-tetrahydro-2-naphthyl)-3-oxopropenyl]benzoic acid, 4-[3-(4-{[1-(4-4-methylphenyl)methanoyl]methylamino}-5,5,8,8-tetramethyl-5,6,7,8-tetrahydro-2-naphthyl)-3-hydroxyprop-1-ynyl]benzoic acid, 4-(3-{4-[1-(4-methylphenyl)-1-methylethoxy]-5,5,8,8-tetramethyl-5,6,7,8-tetrahydro-2-naphthyl}-3-hydroxypropenyl)benzoic acid, 4-(3-{4-[1-(4-methylphenyl)-1-methylethoxy]-5,5,8,8-tetramethyl-5,6,7,8-tetrahydro-2-naphthyl}-3-oxopropenyl)benzoic acid, 4-(3-{4-[1-(4-methylphenyl)-1-methylethoxy]-5,5,8,8-tetramethyl-5,6,7,8-tetrahydro-2-naphthyl}-3-hydroxyprop-1 -ynyl)benzoic acid, 4-{3-[4-(4-dimethylaminobenzylamino)-5,5,8,8-tetramethyl-5,6,7,8-tetrahydro-2-naphthyl]-3-hydroxypropenyl}benzoic acid, 4-(3-{4-[(4-dimethylaminobenzyl)methylamino]-5,5,8,8-tetramethyl-5,6,7,8-tetrahydro-2-naphthyl}-3-oxopropenyl)benzoic acid, 4-{3-[4-(4-dimethylaminobenzylamino)-5,5,8,8-tetramethyl-5,6,7,8-tetrahydro-2-naphthyl]-3-hydroxyprop-1-ynyl}benzoic acid, 4-{3-[4-(4-dimethylaminobenzylamino)-5,5,8,8-tetramethyl-5,6,7,8-tetrahydro-2-naphthyl]-3-oxopropenyl}benzoic acid, 4-(3-{4-[(4-dimethylaminobenzyl)methylamino]-5,5,8,8-tetramethyl-5,6,7,8-tetrahydro-2-naphthyl}-3-hydroxypropenyl)benzoic acid, 4-(3-{4-[(4-dimethylaminobenzyl)methylamino]-5,5,8,8-tetramethyl-5,6,7,8-tetrahydro-2-naphthyl}-3-hydroxyprop-1-ynyl)benzoic acid, 4-{3-[4-(4-dimethylaminobenzylsulfanyl)-5,5,8,8-tetramethyl-5,6,7,8-tetrahydro-2-naphthyl]-3-hydroxypropenyl}benzoic acid, 4-{3-[4-(4-dimethylaminobenzylsulfanyl)-5,5,8,8-tetramethyl-5,6,7,8-tetrahydro-2-naphthyl]-3-oxopropenyl}benzoic acid, 4-{3-[4-(4-dimethylaminobenzylsulfanyl)-5,5,8,8-tetramethyl-5,6,7,8-tetrahydro-2-naphthyl]-3-hydroxyprop-1-ynyl}benzoic acid, 4-{3-[4-(4-dimethylaminobenzylamino)-5,5,8,8-tetramethyl-5,6,7,8-tetrahydro-2-naphthyl]-3-hydroxypropenyl}-2-hydroxybenzoic acid, 4-(3-{4-[(4-dimethylaminobenzyl)methylamino]-5,5,8,8-tetramethyl-5,6,7,8-tetrahydro-2-naphthyl}-3-oxopropenyl)-2-hydroxybenzoic acid, 4-{3-[4-(4-dimethylaminobenzylamino)-5,5,8,8-tetramethyl-5,6,7,8-tetrahydro-2-naphthyl]-3-hydroxyprop-1-ynyl}-2-hydroxybenzoic acid, 4-{3-[4-(4-dimethylaminobenzylamino)-5,5,8,8-tetramethyl-5,6,7,8-tetrahydro-2-naphthyl]-3-oxopropenyl}-2-hydroxybenzoic acid, 4-(3-{4-[(4-dimethylaminobenzyl)methylamino]-5,5,8,8-tetramethyl-5,6,7,8-tetrahydro-2-naphthyl}-3-hydroxypropenyl)-2-hydroxybenzoic acid, 4-(3-{4-[(4-dimethylaminobenzyl)methylamino]-5,5,8,8-tetramethyl-5,6,7,8-tetrahydro-2-naphthyl}-3-hydroxyprop-1-ynyl)-2-hydroxybenzoic acid, 4-{3-[4-(4-dimethylaminobenzylsulfanyl)-5,5,8,8-tetramethyl-5,6,7,8-tetrahydro-2-naphthyl]-3-hydroxypropenyl}-2-hydroxybenzoic acid, 4-{3-[4-(4-dimethylaminobenzylsulfanyl)-5,5,8,8-tetramethyl-5,6,7,8-tetrahydro-2-naphthyl]-3-oxopropenyl}-2-hydroxybenzoic acid, 4-{3-[4-(4-dimethylaminobenzylsulfanyl)-5,5,8,8-tetramethyl-5,6,7,8-tetrahydro-2-naphthyl]-3-hydroxyprop-1-ynyl}-2-hydroxybenzoic acid, 4-{3-[4-(4-dimethylaminobenzyloxy)-5,5,8,8-tetramethyl-5,6,7,8-tetrahydro-2-naphthyl]-3-hydroxypropenyl}-2-hydroxybenzoic acid, 4-{3-[4-(4-dimethylaminobenzyloxy)-5,5,8,8-tetramethyl-5,6,7,8-tetrahydro-2-naphthyl]-3-oxopropenyl}-2-hydroxybenzoic acid, 4-{3-[4-(4-dimethylaminobenzyloxy)-5,5,8,8-tetramethyl-5,6,7,8-tetrahydro-2-naphthyl]-3-hydroxyprop-1-ynyl}-2-hydroxybenzoic acid, 4-[3-(4-{[1-(4-dimethylaminophenyl)methanoyl]amino}-5,5,8,8-tetramethyl-5,6,7,8-tetrahydro-2-naphthyl)-3-hydroxypropenyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-oxopropenyl]benzoic acid, 4-[3-(4-{[1-(4-dimethylaminophenyl)methanoyl]amino}-5,5,8,8-tetramethyl-5,6,7,8-tetrahydro-2-naphthyl)-3-hydroxyprop-1-ynyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-hydroxypropenyl]benzoic acid, 4-[3-(4-{[1-(4-dimethylaminophenyl)methanoyl]amino}-5,5,8,8-tetramethyl-5,6,7,8-tetrahydro-2-naphthyl)-3-oxopropenyl]benzoic acid, 4-[3-(4-{[1-(4-dimethylaminophenyl)methanoyl]methylamino}-5,5,8,8-tetramethyl-5,6,7,8-tetrahydro-2-naphthyl)-3-hydroxyprop-1-ynyl]benzoic acid, 4-(3-{4-[1-(4-dimethylaminophenyl)-1-methylethoxy]-5,5,8,8-tetramethyl-5,6,7,8-tetrahydro-2-naphthyl}-3-hydroxypropenyl)benzoic acid, 4-(3-{4-[1-(4-dimethylaminophenyl)-1-methylethoxy]-5,5,8,8-tetramethyl-5,6,7,8-tetrahydro-2-naphthyl}-3-oxopropenyl)benzoic acid, 4-(3-{4-[1-(4-dimethylaminophenyl)-1-methylethoxy]-5,5,8,8-tetramethyl-5,6,7,8-tetrahydro-2-naphthyl}-3-hydroxyprop-1-ynyl)benzoic acid, 4-(3-{4-[2-(4-fluorophenyl)ethyl]-5,5,8,8-tetramethyl-5,6,7,8-tetrahydro-2-naphthyl}-3-hydroxypropenyl)benzoic acid, 4-(3-{4-[2-(4-fluorophenyl)ethyl]-5,5,8,8-tetramethyl-5,6,7,8-tetrahydro-2-naphthyl}-3-oxopropenyl)benzoic acid, 4-(3-{4-[2-(4-fluorophenyl)ethyl]-5,5,8,8-tetramethyl-5,6,7,8-tetrahydro-2-naphthyl}-3-hydroxyprop-1-ynyl)benzoic acid, 4-(3-{4-[2-(4-fluorophenyl)-2-methylpropyl]-5,5,8,8-tetramethyl-5,6,7,8-tetrahydro-2-naphthyl}-3-hydroxypropenyl)benzoic acid, 4-(3-{4-[2-(4-fluorophenyl)-2-methylpropyl]-5,5,8,8-tetramethyl-5,6,7,8-tetrahydro-2-naphthyl}-3-oxopropenyl)benzoic acid, 4-(3-{4-[2-(4-fluorophenyl)-2-methylpropyl]-5,5,8,8-tetramethyl-5,6,7,8-tetrahydro-2-naphthyl}-3-hydroxyprop-1-ynyl)benzoic acid, 4-(3-{4-[2-(4-methylphenyl)ethyl]-5,5,8,8-tetramethyl-5,6,7,8-tetrahydro-2-naphthyl}-3-hydroxypropenyl)benzoic acid, 4-(3-{4-[2-(4-methylphenyl)ethyl]-5,5,8,8-tetramethyl-5,6,7,8-tetrahydro-2-naphthyl}-3-oxopropenyl)benzoic acid, 4-(3-{4-[2-(4-methylphenyl)ethyl]-5,5,8,8-tetramethyl-5,6,7,8-tetrahydro-2-naphthyl}-3-hydroxyprop-1-ynyl)benzoic acid, 4-(3-{4-[2-(4-methylphenyl)-2-methylpropyl]-5,5,8,8-tetramethyl-5,6,7,8-tetrahydro-2-naphthyl}-3-hydroxypropenyl)benzoic acid, 4-(3-{4-[2-(4-methylphenyl)-2-methylpropyl]-5,5,8,8-tetramethyl-5,6,7,8-tetrahydro-2-naphthyl}-3-oxopropenyl)benzoic acid, 4-(3-{4-[2-(4-methylphenyl)-2-methylpropyl]-5,5,8,8-tetramethyl-5,6,7,8-tetrahydro-2-naphthyl}-3-hydroxyprop-1-ynyl)benzoic acid, 4-(3-{4-[2-(4-dimethylaminophenyl)ethyl]-5,5,8,8-tetramethyl-5,6,7,8-tetrahydro-2-naphthyl}-3-hydroxypropenyl)benzoic acid, 4-(3-{4-[2-(4-dimethylaminophenyl)ethyl]-5,5,8,8-tetramethyl-5,6,7,8-tetrahydro-2-naphthyl}-3-oxopropenyl)benzoic acid, 4-(3-{4-[2-(4-dimethylaminophenyl)ethyl]-5,5,8,8-tetramethyl-5,6,7,8-tetrahydro-2-naphthyl}-3-hydroxyprop-1-ynyl)benzoic acid,
4-(3-{4-[2-(4-dimethylaminophenyl)-2-methylpropyl]-5,5,8,8-tetramethyl-5,6 7,8-tetrahydro-2-naphthyl}-3-hydroxypropenyl)benzoic acid,
4-(3-{4-[2-(4-dimethylaminophenyl)-2-methylpropyl]-5,5,8,8-tetramethyl-5,6,7,8-tetrahydro-2-naphthyl}-3-oxopropenyl)benzoic acid,
4-(3-{4-[2-(4-dimethylaminophenyl)-2-methylpropyl]-5,5,8,8-tetramethyl-5,6,7,8-tetrahydro-2-naphthyl}-3-hydroxyprop-1-ynyl)benzoic acid,
4-{3-[4-(4-fluorobenzyloxy)-5,6,7,8-tetrahydro-2-naphthyl]-3-hydroxypropenyl}benzoic acid,
4-{3-[4-(4-fluorobenzyloxy)-8,8-dimethyl-5,6,7,8-tetrahydro-2-naphthyl]-3-hydroxypropenyl}benzoic acid,
4-{3-[4-(4-fluorobenzyloxy)-5,5-dimethyl-5,6,7,8-tetrahydro-2-naphthyl]-3-hydroxypropenyl}benzoic acid, and mixtures thereof.

17. The bicyclic compound as defined by claim 1, selected from the group consisting of:
4-(3-{4-[(4-fluorobenzyl)methylamino]-5,5,8,8-tetramethyl-5,6,7,8-tetrahydro-2-naphthyl}-3-hydroxyprop-1-ynyl)benzamide,
4-(3-{4-[(4-fluorobenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-fluorobenzyl)methylamino]-5,5,8,8-tetramethyl-5,6,7,8-tetrahydro-2-naphthyl}-3-hydroxyprop-1-ynyl)benzamide,
4-{3-[4-(4-fluorobenzyloxy)-5,5,8,8-tetramethyl-5,6,7,8-tetrahydro-2-naphthyl]-3-hydroxyprop-1-ynyl}benzamide,
4-{3-[4-(4-fluorobenzyloxy)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzyloxy)-5,5,8,8-tetramethyl-5,6,7,8-tetrahydro-2-naphthyl]-3-hydroxyprop-1-ynyl}benzamide,
4-{3-[4-(4-fluorobenzylamino)-5,5,8,8-tetramethyl-5,6,7,8-tetrahydro-2-naphthyl]-3-hydroxyprop-1-ynyl}benzamide,
4-{3-[4-(4-fluorobenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzylamino)-5,5,8,8-tetramethyl-5,6,7,8-tetrahydro-2-naphthyl]-3-hydroxyprop-1-ynyl}benzamide,
4-{3-[4-(4-fluorobenzylsulfanyl)-5,5,8,8-tetramethyl-5,6,7,8-tetrahydro-2-naphthyl]-3-hydroxyprop-1-ynyl}benzamide,
4-{3-[4-(4-fluorobenzylsulfanyl)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-fluorobenzylsulfanyl)-5,5,8,8-tetramethyl-5,6,7,8-tetrahydro-2-naphthyl]-3-hydroxyprop-1-ynyl}benzamide,
N-ethyl-4-(3-{4-[(4-fluorobenzyl)methylamino]-5,5,8,8-tetramethyl-5,6,7,8-tetrahydro-2-naphthyl}-3-hydroxyprop-1-ynyl)-N-methylbenzamide,
N-ethyl-4-{3-[4-(4-fluorobenzyloxy)-5,5,8,8-tetramethyl-5,6,7,8-tetrahydro-2-naphthyl]-3-hydroxyprop-1-ynyl}-N-methylbenzamide,
N-ethyl-4-{3-[4-(4-fluorobenzylamino)-5,5,8,8-tetramethyl-5,6,7,8-tetrahydro-2-naphthyl]-3-hydroxyprop-1-ynyl}-N-methylbenzamide,
N-ethyl-4-{3-[4-(4-fluorobenzylsulfanyl)-5,5,8,8-tetramethyl-5,6,7,8-tetrahydro-2-naphthyl]-3-hydroxyprop-1-ynyl}-N-methylbenzamide,
4-(3-{4-[(4-methylbenzyl)methylamino]-5,5,8,8-tetramethyl-5,6,7,8-tetrahydro-2-naphthyl}-3-hydroxyprop-1-ynyl)benzamide,
4-(3-{4-[(4-methylbenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-methylbenzyl)methylamino]-5,5,8,8-tetramethyl-5,6,7,8-tetrahydro-2-naphthyl}-3-hydroxyprop-1-ynyl)benzamide,
4-{3-[4-(4-methylbenzyloxy)-5,5,8,8-tetramethyl-5,6,7,8-tetrahydro-2-naphthyl]-3-hydroxyprop-1-ynyl}benzamide,
4-{3-[4-(4-methylbenzyloxy)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzyloxy)-5,5,8,8-tetramethyl-5,6,7,8-tetrahydro-2-naphthyl]-3-hydroxyprop-1-ynyl}benzamide,
4-{3-[4-(4-methylbenzylamino)-5,5,8,8-tetramethyl-5,6,7,8-tetrahydro-2-naphthyl]-3-hydroxyprop-1-ynyl}benzamide,
4-{3-[4-(4-methylbenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzylamino)-5,5,8,8-tetramethyl-5,6,7,8-tetrahydro-2-naphthyl]-3-hydroxyprop-1-ynyl}benzamide,
4-{3-[4-(4-methylbenzylsulfanyl)-5,5,8,8-tetramethyl-5,6,7,8-tetrahydro-2-naphthyl]-3-hydroxyprop-1-ynyl}benzamide,
4-{3-[4-(4-methylbenzylsulfanyl)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-methylbenzylsulfanyl)-5,5,8,8-tetramethyl-5,6,7,8-tetrahydro-2-naphthyl]-3-hydroxyprop-1-ynyl}benzamide,
N-ethyl-4-(3-{4-[(4-methylbenzyl)methylamino]-5,5,8,8-tetramethyl-5,6,7,8-tetrahydro-2-naphthyl}-3-hydroxyprop-1-ynyl)-N-methylbenzamide,
N-ethyl-4-{3-[4-(4-methylbenzyloxy)-5,5,8,8-tetramethyl-5,6,7,8-tetrahydro-2-naphthyl]-3-hydroxyprop-1-ynyl}-N-methylbenzamide,
N-ethyl-4-{3-[4-(4-methylbenzylamino)-5,5,8,8-tetramethyl-5,6,7,8-tetrahydro-2-naphthyl]-3-hydroxyprop-1-ynyl}-N-methylbenzamide,
N-ethyl-4-{3-[4-(4-methylbenzylsulfanyl)-5,5,8,8-tetramethyl-5,6,7,8-tetrahydro-2-naphthyl]-3-hydroxyprop-1-ynyl]-N-methylbenzamide,
4-(3-{4-[(4-dimethylaminobenzyl)methylamino]-5,5,8,8-tetramethyl-5,6,7,8-tetrahydro-2-naphthyl}-3-hydroxyprop-1-ynyl)benzamide,
4-(3-{4-[(4-dimethylaminobenzyl)methylamino]-5,5,8,8-tetramethyl-5,6,7,8-tetrahydro-2-naphthyl}-3-hydroxyprop-1-ynyl)-N-hydroxybenzamide,
N-ethyl-4-(3-{4-[(4-dimethylaminobenzyl)methylamino]-5,5,8,8-tetramethyl-5,6,7,8-tetrahydro-2-naphthyl}-3-hydroxyprop-1-ynyl)benzamide,
4-{3-[4-(4-dimethylaminobenzyloxy)-5,5,8,8-tetramethyl-5,6,7,8-tetrahydro-2-naphthyl]-3-hydroxyprop-1-ynyl}benzamide,
4-{3-[4-(4-dimethylaminobenzyloxy)-5,5,8,8-tetramethyl-5,6,7,8-tetrahydro-2-naphthyl]-3-hydroxyprop-1-ynyl}-N-hydroxybenzamide, N-ethyl-4-{3-[4-(4-dimethylaminobenzyloxy)-5,5,8,8-tetramethyl-5,6,7,8-tetrahydro-2-naphthyl]-3-hydroxyprop-1-ynyl}benzamide,
4-{3-[4-(4-dimethylaminobenzylamino)-5,5,8,8-tetramethyl-5,6,7,8-tetrahydro-2-naphthyl]-3-hydroxyprop-1-ynyl}benzamide,
4-{3-[4-(4-dimethylaminobenzylamino)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-dimethylaminobenzylamino)-5,5,8,8-tetramethyl-5,6,7,8-tetrahydro-2-naphthyl]-3-hydroxyprop-1-ynyl}benzamide,
4-{3-[4-(4-dimethylaminobenzylsulfanyl)-5,5,8,8-tetramethyl-5,6,7,8-tetrahydro-2-naphthyl]-3-hydroxyprop-1-ynyl}benzamide,
4-{3-[4-(4-dimethylaminobenzylsulfanyl)-5,5,8,8-tetramethyl-5,6,7,8-tetrahydro-2-naphthyl]-3-hydroxyprop-1-ynyl}-N-hydroxybenzamide,
N-ethyl-4-{3-[4-(4-dimethylaminobenzylsulfanyl)-5,5,8,8-tetramethyl-5,6,7,8-tetrahydro-2-naphthyl]-3-hydroxyprop-1-ynyl}benzamide,
N-ethyl-4-(3-{4-[(4-dimethylaminobenzyl)methylamino]-5,5,8,8-tetramethyl-5,6,7,8-tetrahydro-2-naphthyl}-3-hydroxyprop-1-ynyl)-N-methylbenzamide,
N-ethyl-4-{3-[4-(4-dimethylaminobenzyloxy)-5,5,8,8-tetramethyl-5,6,7,8-tetrahydro-2-naphthyl]-3-hydroxyprop-1-ynyl}-N-methylbenzamide,
N-ethyl-4-{3-[4-(4-dimethylaminobenzylamino)-5,5,8,8-tetramethyl-5,6,7,8-tetrahydro-2-naphthyl]-3-hydroxyprop-1-ynyl}-N-methylbenzamide,
N-ethyl-4-{3-[4-(4-dimethylaminobenzylsulfanyl)-5,5,8,8-tetramethyl-5,6,7,8-tetrahydro-2-naphthyl]-3-hydroxyprop-1-ynyl}-N-methylbenzamide, and mixtures thereof.

18. The bicyclic compound as defined by claim 1, wherein formula (I), $R_1$ is a radical (b) and Q is an oxygen atom.

19. A method for inhibiting RAR receptors, comprising administering to cells in need of such inhibition a thus effective amount of at least one bicyclic compound as defined by claim 1.

20. A regime or regimen for treating a dermatological condition or affliction mediated by RAR receptors, comprising administering to a mammalian organism in need of such treatment a thus effective amount of a bicyclic compound as defined by claim 1.

21. The regime or regimen as defined by claim 20, wherein said dermatological condition or affliction mediated by RAR receptors is a keratinization disorder relating to cell differentiation and proliferation selected from the group consisting of common acne, comedones, polymorphs, acne rosacea, nodulocystic acne, acne conglobata, senile acne, secondary acne, solar acne, medication-related acne and occupational acne.

22. The regime or regimen as defined by claim 20, wherein said dermatological condition or affliction mediated by RAR receptors is a keratinization disorder not related to cell differentiation and proliferation selected from the group consisting of ichthyosis, an ichthyosiform condition, Darier's disease, palmoplantar keratoderma, leukoplakia, a leukoplakiform condition, or cutaneous and mucous (buccal) lichen.

23. The regime or regimen as defined by claim 20, wherein said dermatological condition or affliction mediated by RAR receptors is a dermatological condition or affliction with an inflammatory immunological component selected from the group consisting of psoriasis, whether cutaneous, mucous or ungual, psoriatic rheumatism, cutaneous atopy, eczema, respiratory atopy, and gingival hypertrophy.

24. A regime or regimen for treating dermal or epidermal proliferations mediated by RAR receptors, whether said dermal or epidermal proliferations are benign or malignant and whether or not of viral origin, comprising administering to a mammalian organism in need of such treatment a thus effective amount of a bicyclic compound as defined by claim 1.

25. The regime or regimen as defined by claim 24, wherein said dermal or epidermal proliferations mediated by RAR receptors is selected from the group consisting of common warts, flat warts, verruciform epidermodysplasia, oral or florid papillomatoses, T lymphoma, proliferations induced by ultraviolet radiation, basocellular or spinocellular epithelioma, any cutaneous precancerous lesion and a keratoacanthoma.

26. The regime or regimen as defined by claim 20, wherein said dermatological condition or affliction mediated by RAR receptors is an immune dermatosis selected from the group consisting of lupus erythematosus, an immune bullous or collagen disease, and scleroderma.

27. A regime or regimen for treating a dermatological condition or affliction having an immunological component mediated by RAR receptors, comprising administering to a mammalian organism in need of such treatment a thus effective amount of a bicyclic compound as defined by claim 1.

28. A regime or regimen for treating an ophthalmological disorder or corneopathy mediated by RAR receptors, comprising administering to a mammalian organism in need of such treatment a thus effective amount of a bicyclic compound as defined by claim 1.

29. A regime or regimen for treating the stigmata of epidermal and/or dermal atrophy, or any other form of cutaneous atrophy mediated by RAR receptors, comprising administering to a mammalian organism in need of such treatment a thus effective amount of a bicyclic compound as defined by claim 1.

30. A regime or regimen for treating a cutaneous condition or affliction of viral origin mediated by RAR receptors, comprising administering to a mammalian organism in need of such treatment a thus effective amount of a bicyclic compound as defined by claim 1.

31. A regime or regimen for treating a skin condition or affliction associated with chronological or actinic aging mediated by RAR receptors, comprising administering to a mammalian organism in need of such treatment a thus effective amount of a bicyclic compound as defined by claim 1.

32. The regime or regimen as defined by claim 31, wherein said skin condition or affliction associated with chronological or actinic aging mediated by RAR receptors is selected from the group consisting of excess pigmentation, actinic keratosis and xerosis.

33. A regime or regimen for treating a sebaceous function disorder mediated by RAR receptors, comprising administering to a mammalian organism in need of such treatment a thus effective amount of a bicyclic compound as defined by claim 1.

34. The regime or regimen as defined by claim 20, wherein said dermatological condition or affliction mediated by RAR receptors is selected from the group consisting of hyperseborrhoea of acne and simple seborrhoea.

35. A regime or regimen for preventing or treating a cicatrization disorder, or for preventing or repairing stretch marks, or for promoting cicatrization mediated by RAR receptors, comprising administering to a mammalian organism in need of such treatment a thus effective amount of a bicyclic compound as defined by claim 1.

36. A regime or regimen for treating a skin pigmentation disorder mediated by RAR receptors, comprising administering to a mammalian organism in need of such treatment a thus effective amount of a bicyclic compound as defined by claim 1.

37. The regime or regimen as defined by claim 36, wherein said skin pigmentation disorder mediated by RAR receptors is selected from the group consisting of hyperpigmentation, melasma, hypopigmentation and vitiligo.

38. A regime or regimen for treating a lipid metabolism condition or affliction mediated by RAR receptors, comprising administering to a mammalian organism in need of such treatment a thus effective amount of a bicyclic compound as defined by claim 1.

39. The regime or regimen as defined by claim 38, wherein said dermatological condition or affliction mediated by RAR receptors is selected from the group consisting of obesity, hyperlipidaemia, and non-insulin-dependent diabetes.

40. A regime or regimen for treating an inflammatory condition or affliction mediated by RAR receptors, comprising administering to a mammalian organism in need of such treatment a thus effective amount of a bicyclic compound as defined by claim 1.

41. The regime or regimen as defined by claim 40, wherein said dermatological condition or affliction mediated by RAR receptors is arthritis.

42. A regime or regimen for treating a cancerous or precancerous condition or affliction mediated by RAR receptors, comprising administering to a mammalian organism in need of such treatment a thus effective amount of a bicyclic compound as defined by claim 1.

43. A regime or regimen for treating alopeciamediated by RAR receptors, comprising administering to a mammalian organism in need of such treatment a thus effective amount of a bicyclic compound as defined by claim 1.

44. A regime or regimen for treating a disorder of the immune system mediated by RAR receptors, comprising administering to a mammalian organism in need of such treatment a thus effective amount of a bicyclic compound as defined by claim 1.

45. The regime or regimen as defined by claim 44, wherein said disorder of the immune system mediated by RAR receptors is selected from the group consisting of asthma, type 1 sugar diabetes, multiple sclerosis and selective dysfunction of the immune system.

46. A regime or regimen for treating a condition or affliction of the cardiovascular system mediated by RAR receptors, comprising administering to a mammalian organism in need of such treatment a thus effective amount of a bicyclic compound as defined by claim 1.

47. The regime or regimen as defined by claim 46, wherein said condition or affliction of the cardiovascular system mediated by RAR receptors is selected from the group consisting of arteriosclerosis and hypertension.

48. A pharmaceutical composition comprising a therapeutically effective amount of at least one bicyclic compound as defined by claim 1, or salt or isomer thereof, formulated into aphysiologically acceptable medium therefor.

49. The pharmaceutical composition as defined by claim 48, said at least one bicyclic compound, or salt or isomer, comprising from 0.001% to 10% by weight thereof.

50. The pharmaceutical composition as defined by claim 48, said at least one bicyclic compound, or salt or isomer, comprising from 0.01% to 1% by weight thereof.

51. A cosmetic composition comprising a cosmetic effective amount of at least one bicyclic compound as defined by claim 1, or salt or isomer thereof, formulated into a cosmetically acceptable medium therefor.

52. The cosmetic composition as defined by claim 51, said at least one bicyclic compound, or salt or isomer, comprising from 0.001% to 3% by weight thereof.

53. The pharmaceutical composition as defined by claim 48, formulated as apaste, an ointment, a cream, a milk, a pomade, a powder, an impregnated pad, a syndet, a gel, a spray, a mousse, a stick, a shampoo, microspheres, nanospheres, lipid or polymer vesicles, a controlled release patch, a syrup, tablets, capsules, granules, an emulsion, or a dragee.

* * * * *